United States Patent [19]

Achini et al.

[11] 4,171,369
[45] Oct. 16, 1979

[54] HYDRO-4-PHENYL-BENZ[f]ISOINDOLINE COMPOUNDS

[75] Inventors: Roland Achini, Therwil; Wolfgang Oppolzer, Genève; Emil Pfenninger, Therwil, all of Switzerland

[73] Assignee: Sandoz Ltd., Basel, Switzerland

[21] Appl. No.: 558,931

[22] Filed: Mar. 17, 1975

Related U.S. Application Data

[63] Continuation-in-part of Ser. No. 546,054, Jan. 31, 1975, abandoned, which is a continuation-in-part of Ser. No. 400,434, Sep. 24, 1973, abandoned.

[30] Foreign Application Priority Data

Sep. 29, 1972 [CH] Switzerland ............... 14250/72
Aug. 3, 1973 [CH] Switzerland ............... 11305/73

[51] Int. Cl.² .................. A61K 31/40; C07D209/44
[52] U.S. Cl. .................. 424/274; 260/326.1; 260/561 HL
[58] Field of Search .................. 260/326.1; 424/274

[56] References Cited

U.S. PATENT DOCUMENTS

| | | |
|---|---|---|
| 3,890,347 | 6/1975 | Middlemiss ............ 260/326.1 |
| 3,973,030 | 7/1976 | Bowman et al. ............ 260/326.1 |
| 4,014,899 | 3/1977 | Bowman et al. ............ 260/326.1 |

*Primary Examiner*—Ethel G. Love
*Attorney, Agent, or Firm*—Gerald D. Sharkin; Robert S. Honor; Timothy G. Rothwell

[57] ABSTRACT

The present invention concerns novel hydro-4-phenyl-benz[f]isoindoline derivatives, of the formula

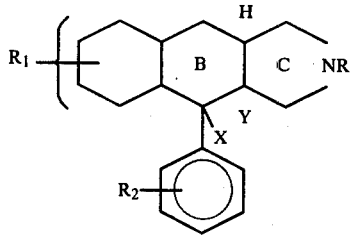

wherein
R is hydrogen or substituted or unsubstituted alkyl,
$R_1$ and $R_2$ are hydrogen, halogen or alkyl, and either
X and Y are hydrogen, or
X and Y together are an additional bond,
useful as analgesics and antidepressants.

106 Claims, No Drawings

HYDRO-4-PHENYL-BENZ[F]ISOINDOLINE COMPOUNDS

This application is a continuation-in-part of our copending application Ser. No. 546,054 filed Jan. 31, 1975, now abandoned which is a continuation-in-part of our earlier copending application Ser. No. 400,434 filed Sept. 24, 1973 now abandoned, the contents of which are hereby incorporated by reference.

The present invention relates to new hydro-4-phenyl-benz[f]isoindoline derivatives.

The present invention provides compounds of formula I,

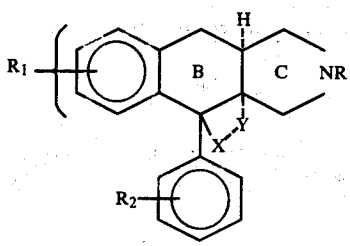

wherein

R is (i) hydrogen, (ii) alkyl of 1 to 5 carbon atoms, (iii) alkenyl or alkynyl of 3 to 5 carbon atoms, the multiple bond thereof being in other than the α-position, (iv) alkyl of 1 to 4 carbon atoms substituted by cycloalkyl of 3 to 6 carbon atoms, (v) hydroxyalkyl of 2 to 5 carbon atoms, (vi) phenylalkyl of 7 to 11 carbon atoms in the aggregate thereof, (vii) phenylalkyl of 7 to 11 carbon atoms in the aggregate thereof monosubstituted in the phenyl thereof by halogen, alkoxy of 1 to 4 carbon atoms or alkyl of 1 to 4 carbon atoms, or (viii) A—CO—$R_3$, wherein A is alkylene of 1 to 4 carbon atoms, and
$R_3$ is alkyl of 1 to 5 carbon atoms, alkoxy of 1 to 4 carbon atoms, hydroxy, phenyl or phenyl substituted by halogen, $R_1$ and $R_2$ are identical of different and each is hydrogen, halogen or alkyl of 1 to 4 carbon atoms, and either (i) each of X and Y is hydrogen, and the rings B and C are cis to each other, or (ii)

X and Y together are an additional bond.

Substituted as used herein preferably signifies monosubstituted. The term lower with reference to a carbon-containing radical and where not particularly defined otherwise, preferably refers to up to 4 carbon atoms.

When the radical R or $R_3$ is lower alkyl of 1 to 5 carbon atoms, then this especially has 1 to 4 preferably 1 to 3, e.g. 1 or 2 carbon atoms.

When R is an alkyl group of 1 to 4 carbon atoms substituted by a cycloalkyl group of 3 to 6 carbon atoms, then the alkyl group thereof especially has 1 to 3, e.g. 1 or 2 carbon atoms and the cycloalkyl group thereof especially has 3 to 5, e.g. 3 carbon atoms. An example of a preferred substituent of this series is the cyclopropylmethyl group.

When the radical R is a hydroxyalkyl group of 2 to 5 carbon atoms, then this especially has 2 to 4, preferably 2 or 3 carbon atoms.

When the radical R is a phenylalkyl radical of 7 to 11 carbon atoms or a phenylalkyl radical of 7 to 11 carbon atoms monosubstituted by halogen, alkoxy of 1 to 4 or alkyl of 1 to 4 carbon atoms, then this phenylalkyl radical especially has 7 to 9, preferably 7 or 7 carbon atoms. A halogen substituent which may be present in this radical especially denotes fluorine, chlorine or bromine, preferably fluorine or chlorine. An alkoxy or alkyl substituent of 1 to 4 carbon atoms which may be present in this radical especially has 1 to 3, preferably 1 or 2 carbon atoms.

When the radical R is a group A—CO—$R_3$, preferably when $R_3$ is other than phenyl or halophenyl then A especially has 1 to 3, preferably 1 or 2 carbon atoms.

When $R_3$ is phenyl substituted by halogen, then the halogen substituent especially signifies fluorine, chlorine or bromine, preferably fluorine or chlorine.

When the radical $R_3$ is an alkoxy group of 1 to 4 carbon atoms, then this especially has 1 or 2, preferably 1 carbon atom.

When the radical $R_1$ or $R_2$ is halogen, then this especially signifies fluorine, chlorine or bromine, preferably fluorine or chlorine.

When the radical $R_1$ or $R_2$ is an alkyl group of 1 to 4 carbon atoms, then this especially has 1 or 2, preferably 1 carbon atom.

X when hydrogen, may be cis or trans to the hydrogen atom in the 9α-position.

Another preferred embodiment of this invention is a compound of the formula

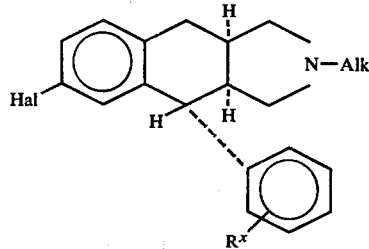

wherein

Hal is halogen and
Alk is alkyl of 1 to 5 carbon atoms, and
$R^x$ is halogen or alkyl of 1 to 4 carbon atoms.

Further, in accordance with the invention, a compound of formula Ia,

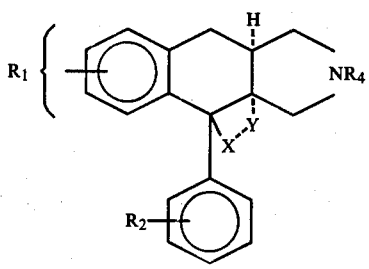

wherein $R_1$, $R_2$, X and Y are as defined above, and
$R_4$ is (i) alkyl of 1 to 5 carbon atoms, (ii) alkenyl or alkynyl of 120°-3 to 5 carbon atoms, the multiple bond thereof being in other than the α-position thereof, (iii) alkyl of 1 to 4 carbon atoms substituted by cycloalkyl of 3 to 6 carbon atoms, (iv) hydroxyalkyl of 2 to 5 carbon atoms, (v) phenylalkyl of 7 to 11 carbon atoms in the aggregate thereof, (vi) phenylalkyl of 7 to 11 carbon atoms in the aggregate thereof monosubstituted in the phenyl thereof by halogen, alkoxy of 1 to 4 carbon atoms or alkyl of 1 to 4 carbon actons, or (vii) A—CO—R₃, wherein A and R₃ are as defined above, may be obtained by a process comprising
(a) alkylating a compound of formula Ib,

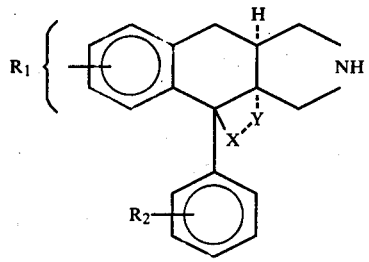

wherein R₁, R₂, X and Y are as defined above, or (b) reductively alkylating a compound of formula Ib, to produce a compound of formula Ie,

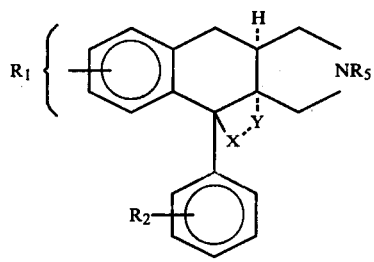

wherein
R₁, R₂, X and Y are as defined above and
R₅ is a primary or secondary alkyl of 1 to 5 carbon atoms, or
(c) epimerising a compound of formula If,

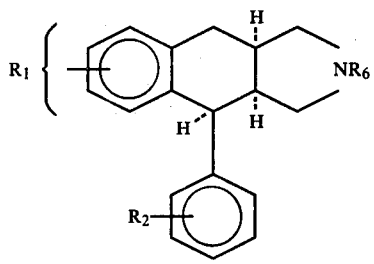

wherein
R₁ and R₂ are as defined above, and
R₆ is (i) alkyl of 1 to 5 carbon atoms, (ii) alkenyl or alkynyl of 3 to 5 carbon atoms, the multiple bond thereof being in other than the α-position thereof, (iii) alkyl of 1 to 4 carbon atoms substituted by cycloalkyl of 3 to 6 carbon atoms, (iv) hydroxyalkyl of 2 to 5 carbon atoms, (v) phenylalkyl of 7 to 11 carbon atoms in the aggregate thereof, (vi) phenylalkyl of 7 to 11 carbon atoms in the aggregate thereof monosubstituted in the phenyl thereof by halogen, alkoxy of 1 to 4 carbon atoms or alkyl of 1 to 4 carbon atoms, or (vii) A—CO—R₃',
wherein
A is as defined above, and
R₃' is alkyl of 1 to 5 carbon atoms, phenyl or phenyl substituted by halogen, under strong alkaline conditions to produce a compound of formula Ig,

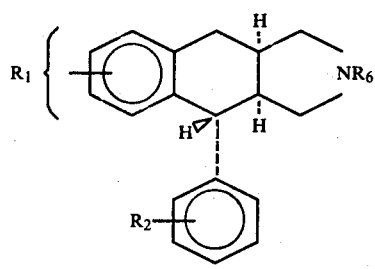

wherein R₁, R₂ and R₆ are as defined above, or
(d) hydrogenating a compound of formula Ih,

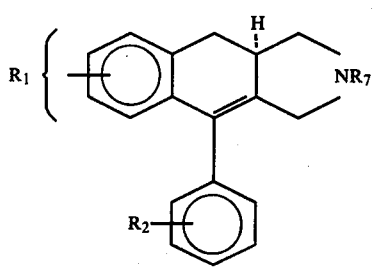

wherein
R₁ and R₂ are as defined above, and
R₇ is (i) alkyl of 1 to 5 carbon atoms, (ii) alkyl of 1 to 4 carbon atoms substituted by cycloalkyl of 3 to 6 carbon atoms, (iii) phenylalkyl of 7 to 11 carbon atoms in the aggregate thereof, (iv), phenylalkyl of 7 to 11 carbon atoms in the aggregate thereof by halogen or alkyl of 1 to 4 carbon atoms, or (iv) A—CO—R₃,
wherein A and R₃ are as defined above,
with hydriodic acid and red phosphorus to produce a compound of formula Ii,

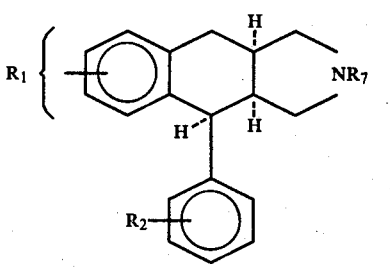

wherein R₁, R₂ and R₇ are as defined above, or
(e) catalytically hydrogenating a compound of formula Ij,

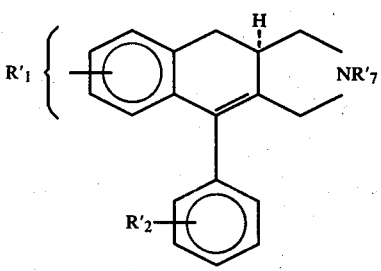

wherein $R_1'$ and $R_2'$ are identical or different and each is hydrogen, fluorine or alkyl of 1 to 4 carbon atoms, and $R_7'$ is (i) alkyl of 1 to 5 carbon atoms, (ii) alkyl of 1 to 4 carbon atoms substituted by cycloalkyl of 3 to 6 carbon atoms, (iii) hydroxyalkyl of 2 to 5 carbon atoms, (iv) phenylalkyl of 8 to 11 carbon atoms in the aggregate thereof, the phenyl thereof being in other than the α-position of the alkyl moiety or (v) phenylalkyl of 8 to 11 carbon atoms in the aggregate thereof monosubstituted in the phenyl thereof by halogen, alkoxy of 1 to 4 carbon atoms or alkyl of 1 to 4 carbon atoms, the phenyl thereof being in other than the α-position of the alkyl moiety, to produce a compound of formula Ik,

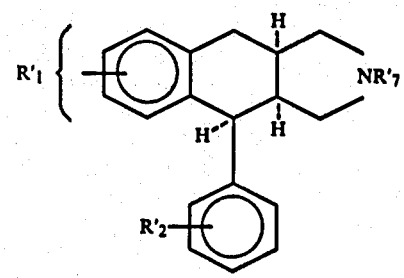

wherein $R_1'$, $R_2'$ and $R_7'$ are as defined above, or (f) reducing with a metal hydride a compound of formula II,

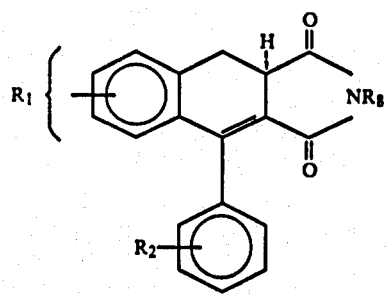

wherein $R_1$ and $R_2$ are as defined above and, $R_8$ is (i) alkyl or 1 to 5 carbon atoms, (ii) alkyl of 1 to 4 carbon atoms substituted by cycloalkyl of 3 to 6 carbon atoms, (iii) hydroxyalkyl of 2 to 5 carbon atoms, (iv) phenylalkyl of 7 to 11 carbon atoms in the aggregate thereof, (v) phenylalkyl of 7 to 11 carbon atoms in the aggregate thereof monosubstituted on the phenyl thereof by halogen, alkoxy of 1 to 4 carbon atoms or alkyl of 1 to 4 carbon atoms, to produce a compound of formula Iu,

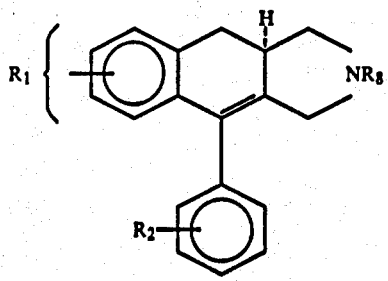

wherein $R_1$, $R_2$ and $R_8$ are as defined above, or (g) reducing a compound of formula IV,

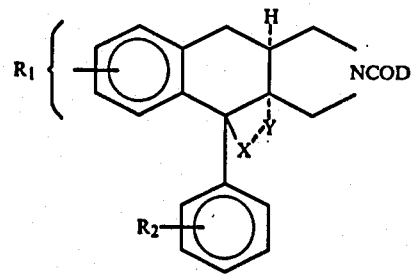

wherein $R_1$, $R_2$, X and Y are as defined above, and

D is (i) hydrogen, (ii) alkyl of 1 to 4 carbon atoms, (iii) cycloalkyl of 3 to 6 carbon atoms, (iv) alkyl of 1 to 3 carbon atoms substituted by cycloalkyl of 3 to 6 carbon atoms, (v) hydroxyalkyl of 1 to 4 carbon atoms, (vi) phenyl, (vii) phenylalkyl of 7 to 10 carbon atoms in the aggregate thereof, (viii) phenyl monosubstituted by halogen, alkoxy of 1 to 4 carbon atoms or alkyl of 1 to 4 carbon atoms, or (ix) phenylalkyl of 7 to 10 carbon atoms in the aggregate thereof monosubstituted on the phenyl thereof by halogen, alkoxy of 1 to 4 carbon atoms or alkyl of 1 to 4 carbon atoms, to produce a compound of formula Im,

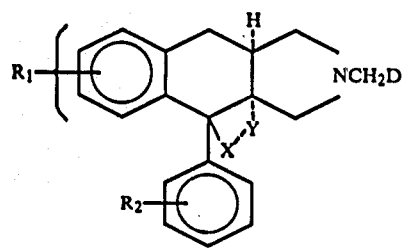

wherein $R_1$, $R_2$, X, Y and D are as defined above, with a metal hydride, or (h) hydrolyzing a compound of formula Ic,

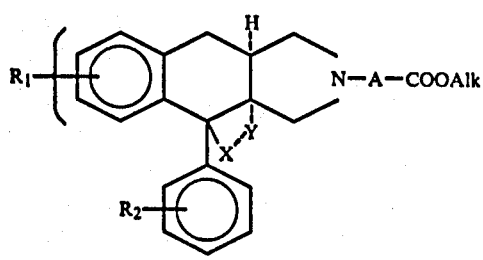

wherein $R_1$, $R_2$, X, Y and A are as defined above, and

Alk is alkyl of 1 to 4 carbon atoms, to produce a compound of formula Id,

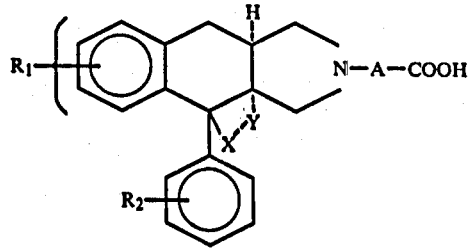

wherein $R_1$, $R_2$, X, Y and A are as defined above.

Process variants (a) to (h) may for example be effected as follows:

(a) N-alkylation of a compound of formula Ib may, for example, be effected with compound of formula V $$ER_4 \qquad\qquad V$$

wherein
$R_4$ is as defined above, and
E is the acid radical of a reactive ester.

In the compounds of formula V, E may, for example, signify halogen such as chlorine, bromine or iodine or the acid radical of an organic sulphonic acid, e.g. an alkylsulphonyloxy radical preferably of 1 to 4 carbon atoms such as methylsulphonyloxy or an arylsulphonyloxy radical such as phenylsulphonyloxy or tolylsulphonyloxy.

The N-alkylation of a compound of formula Ib with a compound of formula V is conveniently effected in an organic solvent, e.g. an amide of an aliphatic carboxylic acid preferably of 1 to 4 carbon atoms, e.g. dimethylformamide. The reaction is conveniently affected in the presence of a basic condensation agent such as sodium carbonate or N-ethyl-N,N-diisopropylamine.

The reaction temperature may be from room temperature to about 100° C.

Suitable reactive derivatives corresponding to a compound of formula V may alternatively be employed, inter alia, $\alpha,\beta$-unsaturated carbonyl compounds for the introduction of a radical $A^I$—CO—$R_3$, wherein $A^I$ is ethylene or alkyl substituted ethylene and $R_3$ is as defined above, and, e.g., ethylene oxide for the introduction of a e.g. hydroxyethyl group.

The reaction of a compound of formula Ib with an $\alpha,\beta$-unsaturated carbonyl compound such as methylvinylketone or an acrylic acid alkyl ester, the alkoxy group thereof being of 1 to 4 carbon atoms, is conveniently effected in a suitable organic solvent, e.g. a lower alkanol such as methanol or ethanol. The reaction temperature may be from room temperature to the reflux temperature of the reaction mixture, preferably at about 40 to 80° C. Benzyl trimethyl ammonium hydroxide may conveniently be present.

The reaction of a compound of formula Ib with ethylene oxide may be effected in a manner analogous to known methods and is illustrated in Example 5. The reaction may be effected in an inert solvent, e.g. ethanol.

(b) The reductive alkylation of a compound of formula Ib to a compound of formula Ie may be effected in a manner analogous to known methods, for example, by alkylating a compound of formula Ib with an aldehyde or ketone in the presence of formic acid (Leuckart-Wallach method). Alternatively the reductive alkylation may be effected hydrogenolytically, i.e. with hydrogen gas in the presence of a suitable metal catalyst such as raney-nickel or palladium. However, under catalytic hydrogenation, any chlorine, bromine or iodine substituents present in the compounds of formula Ib and any additional bond in the 3a, 4-position of the compounds of formula Ib may also be at least partially reduced. Therefore, it is convenient to use the Leuckart-Wallach method indicated above for the reductive alkylation of such compounds, for the production of compounds of formula Ie having chlorine, bromine or iodine substituents.

The reaction in accordance with Leuckart-Wallach may be effected in a suitable organic solvent, preferably an excess of formic acid, at e.g. an elevated temperature, conveniently at reflux.

The catalytic reductive alkylation may be effected in a suitable organic solvent, e.g. an alkanol such as methanol, conveniently at room temperature.

(c) The conversion of a compound of formula If into a compounds of formula Ig may be effected under strong alkaline conditions, e.g. with a strong base, for example potassium tert.butylate. An elevated temperature may be employed, e.g. 100° to 200° C.

Especially suitable reaction media for this conversion are a saturated solution of potassium hydroxide (e.g. 40%) in n-butanol (e.g. 1 to 7 days at reflux temperature) or of potassium tert.butylate in dimethylsulphoxide (e.g. 1 to 7 days at 25°-80° C.), as illustrated in the Examples hereinafter.

Process (c) is especially suited for production of compounds of formula Ig, wherein the radical $R_6$ is alkyl of 1 to 5 carbon atoms, alkynyl or alkenyl of 4 to 5 carbon atoms and wherein the multiple bond is not in an $\alpha$- or $\beta$-position to the nitrogen atom to which $R_6$ is bound, alkyl of 1 to 4 carbon atoms substituted by cycloalkyl of 3 to 6, preferably 5 or 6 carbon atoms, hydroxyalkyl of 2 to 5 carbon atoms, phenylalkyl of 7 to 11 carbon atoms, phenylalkyl of 7 to 11 carbon atoms monosubstituted on the phenyl radical by halogen, alkoxy of 1 to 4 carbon atoms or alkyl of 1 to 4 carbon atoms, or a radical A—CO—$R_3'$, wherein A is as defined above and $R_3'$ is phenyl or phenyl substituted by halogen.

(d) The hydrogenolysis of a compound of formula Ih to a compound of formula Ii with hydroiodic acid and red phosphorus may be effected in a manner analogous to known methods. For example, by adding dropwise an aqueous solution of hydroiodic acid to a solution or suspension of a mixture of a compound of formula Ih with red phosphorus in a suitable solvent or suspension agent such as glacial acetic acid. The resulting reaction mixture may then conveniently be heated, e.g. to 80°-120° C.

(e) The catalytic hydrogenation of a compound of formula Ij to a compound of formula Ik may be effected in a manner analogous to known methods.

Suitable catalysts are metal catalysts such as palladium and raney-nickel. The hydrogenation may be effected in an organic solvent, e.g. a lower alkanol such as methanol or ethanol.

The reaction is preferably effected at a slight excess pressure, e.g. about 2 to 6 atmospheres and preferably at an elevated temperature, e.g. from about 40° to about 80° C.

In accordance with a preferred method, the hydrogenation is effected in the presence of a palladium catalyst produced in situ from palladium (II)-chloride and sodium borohydride.

(f) The reduction of a compound of formula II with metal hydride may be effected in a manner analogous to the methods known for the reduction of amides.

This may, for example, be effected by adding a solution of aluminium hydride or a dialkyl aluminium hydride in an inert organic solvent, e.g. a cyclic or open chain ether such as tetrahydrofuran, to a solution of a compound of formula II in preferably the same inert organic solvent and conveniently at room or elevated temperature. The reduction may, for example, also be effected with a lithium aluminium hydride/aluminium chloride mixture. When the compounds of formula II do not have a chlorine, bromine or iodine substituent, then the reduction may also be effected with a complex hydride, e.g. a complex aluminium hydride such as lithium aluminium hydride or with a complex lithium aluminium hydride - aluminium chloride. This process variant may be effected under process conditions analogous to those described for the reduction with aluminium hydride.

(g) The reduction of an amide of formula IV with a metal hydride may also be effected in a manner analogous to known methods. Suitable metal hydrides are, for example, aluminium hydride and dialkyl aluminium hydride and, when the compounds of formula IV do not have a chlorine, bromine or iodine substituent, then also lithium aluminium hydride or lithium aluminium hydride/aluminium chloride. Suitable solvents are inert solvents e.g. cyclic or open chain ether such as tetrahydrofuran.

The reduction may be effected at room temperature.

(h) A hydrolysis of a compound of formula Ic may be effected under acid conditions, e.g. with 2 N hydrochloric acid, conveniently at an elevated temperature, preferably at reflux temperature.

However, a compound of formula Ic may by hydrolyzed to a compound of formula Id under alkaline conditions. The alkaline hydrolysis is preferably effected in an aqueous alcoholic solution of an alkaline metal or alkaline earth metal hydroxide, especially in an aqueous, methanolic or ethanolic solution of sodium, potassium or barium hydroxide, conveniently at room temperature or at a slightly elevated temperature.

The compounds of formula Ia obtained in accordance with the above processes may be isolated and purified in accordance with known methods.

Further, in accordance with the invention, a compound of formula Ib may be obtained by a process comprising (a') replacing the group $R_9$ by a hydrogen atom in a compound of formula VI,

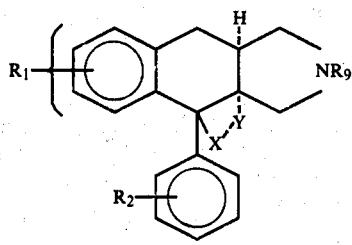

wherein
$R_1$, $R_2$, X and Y are as defined above, and
$R_9$ is an electron attracting group, or (b') epimerising a compound of formula VII,

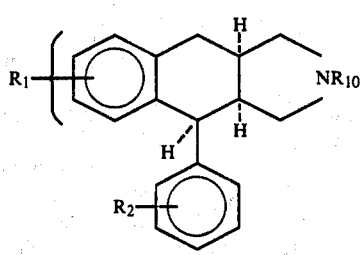

wherein
$R_1$ and $R_2$ are as defined above, and $R_{10}$ is the radical $R_9$, defined above, under strong alkaline conditions, to produce a compound of formula In

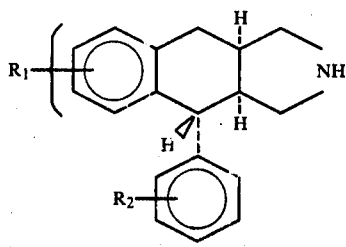

wherein $R_1$ and $R_2$ are as defined above, or P (c') catalytically hydrogenating a compound of formula Io

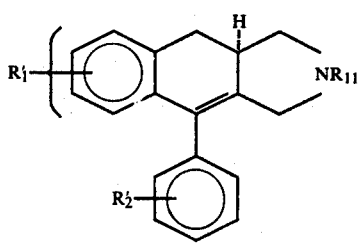

wherein
$R_1'$ and $R_2'$ are as defined above, and
$R_{11}$ is hydrogen or the benzyl group,
to produce a compound of formula Ip,

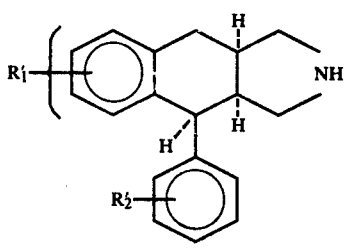

wherein $R_1'$ and $R_2'$ are as defined above, or (d') reducing a compound of formula VIII

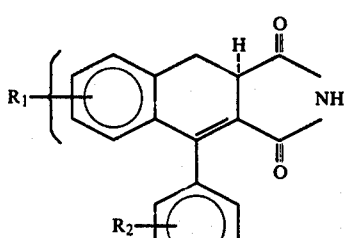

wherein $R_1$ and $R_2$ are as defined above, with a metal hydride to produce a compound of formula Iq,

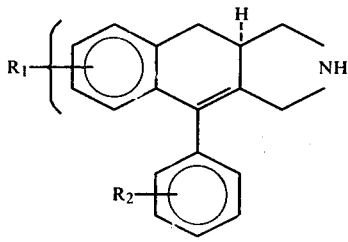

Iq, wherein $R_1$ and $R_2$ are as defined above.

Process variants ($a^l$) to ($d^l$) may be effected as follows:

($a^l$) Examples of suitable electron-attracting groups $R_9$ are acyl groups such as the trifluoroacetyl group, the benzoyl group, an aliphatic or aromatic sulphonyl group, e.g. a tosyl radical, a lower alkoxy-carbonyl radical such as the methoxy- or ethoxy-carbonyl group, or the phenoxycarbonyl group.

The removal of the group $R_9$ may, for example, be effected by hydrolysis with a 1 to about 5 N-solution of an alkali metal hydroxide such as sodium or potassium hydroxide in a lower alkanol, preferably methanol or ethanol.

When $R_9$ is an acyl group which can be readily split off, e.g. the trifluoroacetyl group, then hydrolysis may be effected at room temperature or at a slightly elevated temperature.

When $R_9$ is an acyl group which is less readily split off, e.g. the phenoxy carbonyl group, then the reaction is conveniently effected with heating, preferably at the reflux temperature of the reaction mixture.

When $R_9$ is an aliphatic or aromatic sulphonyl group, then this group may be split off under reductive conditions, in a manner analogous to known methods, e.g. with sodium ammonia or phenol in e.g. 40% hydrobromic acid.

The hydrolysis of a compound of formula VI may also be effected under acid conditions, e.g. with 2 N-hydrochloric acid, conveniently at an elevated temperature, preferably at the reflux temperature of the reaction mixture.

($b^l$) The conversion of a compound of formula VII into a compound of formula In may be effected as described for the conversion of a compound of formula If into a compound of formula Ig (see process c).

Any group $R_9$ which may be present, will be split off in the presence of nucleophilic anions, e.g. OH$\ominus$, O-(lower)alkyl$\ominus$.

($c^l$) The catalytic hydrogenation of a compound of formula Io may be effected as described for the catalytic hydrogenation of a compound of formula Ij (see process e).

When $R_{11}$ is the benzyl group, then this may be also removed.

($d^l$) The reduction of a compound of formula VIII with a metal hydride may be effected as described for the reduction of a compound of formula II to a compound of formula Iu (process f).

The compounds of formulae II, IV, VI and VIII are also new.

A compound of formula II may, for example, be obtained by condensing a compound of formula X,

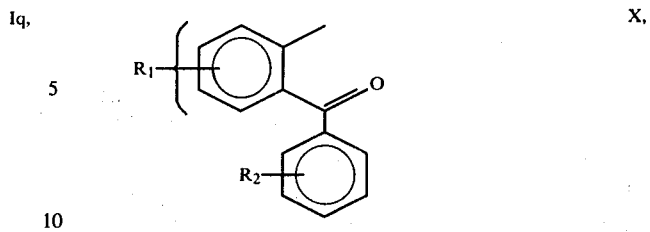

X, wherein $R_1$ and $R_2$ are as defined above, with a compound of formula XI,

XI, wherein $R_8$ is as defined above, to produce a compound of formula XII

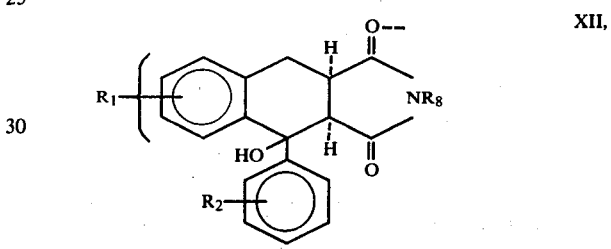

XII, wherein $R_1 R_2$ and $R_8$ are as defined above, and dehydrating the resulting compound of formula XII.

The condensation of a compound of formula X with a compound of formula XI may be effected, e.g. by irradiation of a solution of these compounds in an inert solvent such as acetone or a chlorinated aliphatic hydrocarbon such as methylene chloride, at e.g. room temperature.

The compounds of formula XII may be dehydrated in accordance with known methods with an organic or inorganic acid. Examples of suitable organic acids are aliphatic or aromatic sulphonic acid, trifluoracetic acid, trichloracetic acid and formic acid and examples of suitable inorganic acids are sulphuric acid, hydrochloric acid, perchloric acid and phosphoric acid.

While the removal of water generally proceeds smoothly at room temperature when a concentrated strong acid, such as sulphuric acid or trifluoracetic acid is used, it is advisable to heat the reaction mixture when a dilute or weaker acid is used.

Dehydration may be effected, e.g. by dissolving the compound of formula XII in an organic acid such as trifluoracetic acid and stirring the reaction mixture at a temperature of e.g. about 20° to 40° C.

The compounds of formula IV and the compounds of formula VI may be produced in accordance with known methods by acylating the corresponding compounds of formula Ib, e.g. with a corresponding acid halide, preferably a corresponding chloride or bromide, or with a corresponding acid anhydride. N-formylation may be alternatively effected in accordance with known methods. Most of the compounds of formula VI may be synthesized directly, as described below, by cyclisation of a suitable amide.

($a^{II}$) A compound of formula VIa

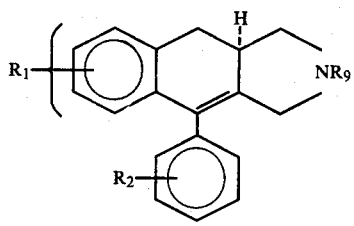

wherein $R_1$, $R_2$ and $R_9$ are as defined above, may be obtained by thermic cyclisation of a compound of formula XIII

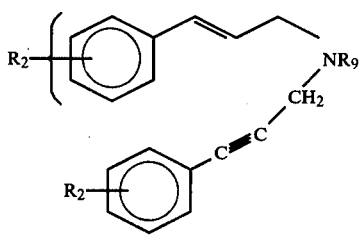

wherein $R_1$, $R_2$ and $R_9$ are as defined above.

The thermic cyclisation of a compound of formula XIII may be effected in an inert organic solvent, preferably having a high boiling point, e.g. dichlorobenzene. The reaction is conveniently effected in the absence of oxygen and the reaction mixture is heated to about 160°–190° C.

The resulting compound of formula VIa may be de-acylated to the corresponding NH-compound, as described above, and, if desired, subjected to catalytic hydrogenation. In the latter case, any chlorine, bromine or iodine substituent which may be present may also be partially reduced.

($b^{II}$) A compound of formula VIb

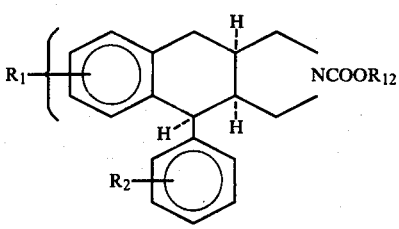

wherein
$R_1$ and $R_2$ are as defined above, and
$R_{12}$ is lower alkyl or a phenyl group,
may, for example, be produced by reduction of a compound of formula Ir

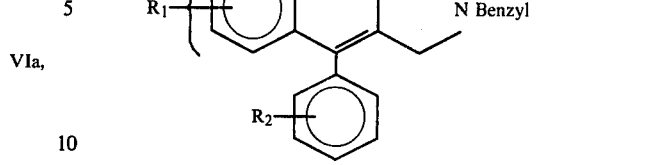

wherein $R_1$ and $R_2$ are as defined above with hydriodic acid and red phosphorus, and subsequent replacement of the benzyl group in the resulting compound of formula Is

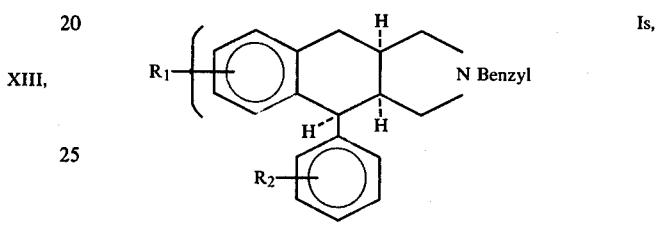

wherein $R_1$ and $R_2$ are as defined above, by a —COOR$_{12}$ group wherein $R_{12}$ is as defined above.

The substitution of the benzyl group in the compound of formula Is may be effected in accordance with known methods, e.g. by reaction of the compound of formula Is with a corresponding chlorocarbonic acid ester.

The resulting compound of formula VIb may be converted, as described (process $a^I$ or $b^I$) into the corresponding tetrahydro compound of formula VII ($R_{10}$=H), or into a compound of formula In.

($c^{II}$) Thermic cyclisation of a compound of formula XIV

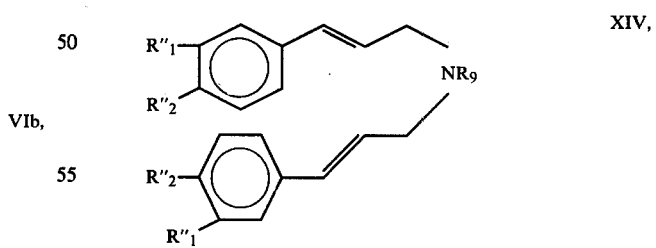

wherein
$R_9$ is as defined above, and
$R_1''$ is hydrogen, and
$R_2''$ is halogen or an alkyl group of 1 to 4 carbon atoms
or $R_1''$ is halogen or alkyl of 1 to 4 carbon atoms, and
$R_2''$ is hydrogen,
yields a compound of formula VIc

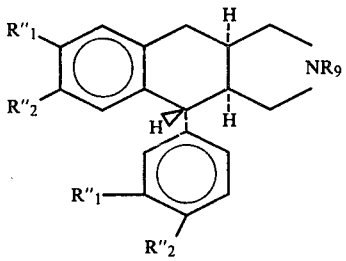

VIc, wherein $R_1''$, $R_2''$ and $R_9$ are as defined above.

The thermic cyclisation of a compound of formula XIV may be effected under the conditions described for process a$^{II}$.

A compound of formula VIII may be produced as described for the production of compounds of formula II, from a compound of formula X and using maleic imide in place of a compound of formula XI.

The compounds of formula Ir are included in the general formula Iu. A process for their production is described inter alia in process f.

The compounds produced in accordance with the above processes may be isolated in the usual manner and purified in accordance with known methods.

Insofar as the production of the starting materials is not described, these are known or may be produced in accordance with known processes or in a manner analogous to the processes described herein or to known processes. For example a compound of formula XIV may be prepared as described in Example 6 in conventional manner.

Free base forms of the compounds of formula I may be converted into acid addition salt forms in conventional manner, and vice versa. Suitable acids for salt formation include hydrochloric acid naphthalene-1,5-disulphuric acid, maleic acid, fumaric acid, hydrobromic acid and sulphuric acid.

Similar considerations apply to other free bases mentioned above.

The compounds of formulae I, II, IV, VI to VIII and XII may be in racemic form or individual optical isomer form, e.g. owing to the presence of an assymetric carbon atom at the 4-position. An individual optical isomer may be obtained from the corresponding racemic mixture in conventional manner, for example by fractional crystallization of salts of the racemic acids with optically active acids.

In the following non-limitative Examples all temperatures are indicated in degrees Centigrade and are uncorrected.

EXAMPLE 1

(3aRS,4SR,9aSR)-2-acetonyl-3a,4,9,9a-tetrahydro-4-phenyl-benz[f]isoindoline [process (a)]

A solution of 3.76 g of chloroacetone in 35 cc of dimethyl formamide is added dropwise at 100° with stirring to a mixture of 10 g of (3aRS,4SR,9aSR)-3a,4,9,9a-tetrahydro-4-phenyl-benz[f]isoindoline, 8.5 g of sodium carbonate, 0.2 g of sodium iodide and 80 cc of dimethyl formamide. The reaction mixture is stirred at 100° for 2 hours and is then concentrated by evaporation in a high vacuum. The residue is shaken with methylene chloride/2N caustic soda solution. The organic phase is dried and concentrated by evaporation, active charcoal is added to the residue in ether, the solution is filtered and concentrated by evaporation, and the residue is crystallized from ether/pentane, whereby the title compound, having a M.P. of 106°-108°, is obtained.

The production of (3aRS,4SR,9aSR)-3a,4,9,9a-tetrahydro-4-phenyl-benz[f]isoindoline is described inter alia in Example 6.

The following compounds of formula Ia are obtained in a manner analogous to that described in Example 1, with the use of the corresponding starting materials, by alkylation of compounds of formula Ib [in accordance with process (a)]:

(3aRS,4SR,9aSR)-3a,4,9,9a-tetrahydro-2-methyl-4-phenyl-benz[f]isoindoline, M.P. of the hydrochloride salt form 207°-209°;

(3aRS,4SR,9aSR)-2-allyl-3a,4,9,9a-tetrahydro-4-phenyl-benz[f]isoindoline, M.P. of the hydrochloride salt form 187°-190°;

(3aRS,4SR,9aSR)-2-cyclopropylmethyl-3a,4,9,9a-tetrahydro-4-phenyl-benz[f]isoindoline, M.P. 65°-68°;

(3aRS,4SR,9aSR)-3a,4,9,9a-tetrahydro-2-isopropyl-4-phenyl-benz[f]isoindoline, M.P. of the hydrogen maleate salt form 150°-158°;

(3aRS,4SR,9aSR)-3a,4,9,9a-tetrahydro-4-phenyl-2-(2-propinyl)benz[f]isoindoline, M.P. 93-95°;

(3aRS,4SR,9aSR)-2-(o-chlorophenethyl)-3a,4,9,9a-tetrahydro-4-phenyl-benz[f]isoindoline, M.P. of the hydrogen maleate form 178°-179°;

(3aRS,4SR,9aSR)-2-(3a,4,9,9a-tetrahydro-4-phenyl-benz-[f]isoindolin-2-yl)acetophenone, M.P. 120°-130°;

(3aRS,4SR,9aSR)-p-fluoro-4-(3a,4,9,9a-tetrahydro-4-phenyl-benz[f]isoindolin-2-yl)butyrophenone, M.P. 81°-84°;

(3aRS,4SR,9aSR)-3a,4,9,9a-tetrahydro-2-(p-methylbenzyl)-4-phenyl-benz[f]isoindoline, M.P. 120°-121°;

(3aRS,4SR,9aSR)-3a,4,9,9a-tetrahydro-2-(p-methoxybenzyl)-4-phenyl-benz[f]isoindoline, M.P. 95°-100°;

(3aRS,4SR,9aSR)-6-chloro-3a,4,9,9a-tetrahydro-2-methyl-4-(4-chlorophenyl)benz[f]isoindoline, M.P. 133°-135°;

(3aRS,4SR,9aSR)-6-chloro-4-(4-chlorophenyl)-2-cyclopropylmethyl-3a,4,9,9a-tetrahydro-benz[f]isoindoline, M.P. 124°-126°;

(3aRS,4SR,9aSR)-2-acetonyl-6-chloro-4-(4-chlorophenyl)-3a,4,9,9a-tetrahydro-benz[f]isoindoline, M.P. of the bis(base)naphthalene-1,5-disulphonate salt form 305°-307°;

(3aRS,4SR,9aSR)-7-chloro-4-(m-chlorophenyl)-3a,4,9,9a-tetrahydro-2-methyl-benz[f]isoindoline, M.P. of the bis(base)naphthalene-1,5-disulphonate salt form 244°-248°;

(3aRS,4SR,9aSR)-2-acetonyl-7-chloro-4-(m-chlorophenyl)-3a,4,9,9a-tetrahydro-benz[f]isoindoline, M.P. of the bis(base)naphthalene-1,5-disulphonate salt form 266°-269°;

(3aRS,4SR,9aSR)-7-chloro-4-(m-chlorophenyl)-2-cyclopropylmethyl-3a,4,9,9a-tetrahydro-benz[f]isoindoline, M.P. of the bis(base)naphthalene-1,5-disulphonate salt form 243°-247°;

(3aRS,4SR,9aSR)-3a,4,9,9a-tetrahydro-2,6-dimethyl-4-(p-tolyl)benz[f]isoindoline, M.P. of bis(base) naphthalene-bis(base) haphthalene-1,5-disulphonate salt form 195°-198°;

(3aRS,4SR,9aSR)-2-cyclopropylmethyl-3a,4,9,9a-tetrahydro-6-methyl-4-(p-tolyl)benz[f]isoindoline, M.P. 98°-100°;

(3aRS,4SR,9aSR)-3a,4,9,9a-tetrahydro-6-methyl-2-(3-methyl-but-2-enyl)-4-(p-tolyl)benz[f]isoindoline, M.P. of the hydrochloride salt form 197°–207° (decomp.);

(3aRS,4SR,9aSR)-3a,4,9,9a-tetrahydro-2,6-dimethyl-4-phenyl-benz[f]isoindoline, M.P. of the bis(base) naphthalene-1,5-disulphonate salt form 280°–283°;

(3aRS,4SR,9aSR)-2-acetonyl-3a,4,9,9a-tetrahydro-6-methyl-4-phenyl-benz[f]isoindoline, M.P. of the bis(base)naphthalene-1,5-disulphonate salt form 295°–301°;

(3aRS,4SR,9aSR)-2-cyclopropylmethyl-3a,4,9,9a-tetrahydro-6-methyl-4-phenyl-benz[f]isoindoline, M.P. of the hydrochloride salt form 198°–204°;

(3aRS,4SR,9aSR)-3a,4,9,9a-tetrahydro-2,7-dimethyl-4-phenyl-benz[f]isoindoline, M.P. of the bis(base) naphthalene-1,5-disulphonate salt form 244°–248°;

(3aRS,4SR,9aSR)-2-acetonyl-3a,4,9,9a-tetrahydro-7-methyl-4-phenyl-benz[f]isoindoline, M.P. of the bis(base naphthalene-1,5-disulphonate salt form 295°–299°;

(3aRS,4SR,9aSR)-2-cyclopropylmethyl-3a,4,9,9a-tetrahydro-7-methyl-4-phenyl-benz[f]isoindoline, M.P. 79°–82°;

2-(3aRS,4SR,9aSR)-3a,4,9,9a-tetrahydro-7-methyl-4-phenyl-benz[f]isoindolin-2-yl)-p-fluoroacetophenone, M.P. of the hydrogen maleate salt form 164°–166°;

(3aRS,4SR,9aSR)-6-chloro-3a,4,9,9a-tetrahydro-2-methyl-4-phenyl-benz[f]isoindoline, M.P. of the hydrochloride salt form 231°–233°;

(3aRS,4SR,9aSR)-3a,4,9,9a-tetrahydro-2-(3-methylbut-2-enyl)-4-phenyl-benz[f]isoindoline (MP of the hydrogen maleate: 163°–168°)

(3aRS,4SR,9aSR)-3a,4,9,9a-tetrahydro-6-methyl-2-(3-methylbut-2-enyl)-4-phenyl-benz[f]isoindoline (3aRS,4SR,9aSR)-3a,4,9,9a-tetrahydro-6-methyl-4-phenyl-2-(2-propinyl)-benz[f]isoindoline (3aRS,4SR,9aSR)-6-chloro-2-cyclopropylmethyl-3a,4,9,9a-tetrahydro-4-phenyl-benz[f]isoindoline (3aRS,4SR,9aSR)-6-chloro-3a,4,9,9a-tetrahydro-4-phenyl-2-(2-propinyl)-benz[f]isoindoline (3aRS,4SR,9aSR)-6-chloro-3a,4,9,9a-tetrahydro-2-(3-methylbut-2-enyl)-4-phenyl-benz[f]isoindoline (3aRS,4SR,9aSR)-6-chloro-2-ethyl-3a,4,9,9a-tetrahydro-4-phenyl-benz[f]isoindoline (3aRS,4SR,9aSR)-2-n-butyl-6-chloro-3a,4,9,9a-tetrahydro-4-phenyl-benz[f]isoindoline (3aRS,4SR,9aSR)-6-chloro-2-isopropyl-3a,4,9,9a-tetrahydro-4-phenyl-benz[f]isoindoline (3aRS,4SR,9aSR)-2-(but-2-inyl)-3a,4,9,9a-tetrahydro-4-phenyl-benz[f]isoindoline (3aRS,4RS,9aSR)-3a,4,9,9a-tetrahydro-2-methyl-4-phenyl-benz[f]isoindoline, M.P. of the bis(base)naphthalene-1,5-disulphonate salt form 297°–303°;

(3aRS,4RS,9aSR)-2-acetonyl-3a,4,9,9a-tetrahydro-4-phenyl-benz[f]isoindoline, M.P. of the bis(base)naphthalene-1,5-disulphonate salt form 265°–269°;

(3aRS,4RS,9aSR)-3a,4,9,9a-tetrahydro-2,6-dimethyl-4-phenyl-benz[f]isoindoline, M.P. of the bis(base)naphthalene-1,5-disulphonate salt form 183°–187°;

(3aRS,4RS,9aSR)-3a,4,9,9a-tetrahydro-2,7-dimethyl-4-phenyl-benz[f]isoindoline, M.P. of the bis(base)naphthalene-1,5-disulphonate salt form 204°–207°;

(3aRS,4RS,9aSR)-2-benzyl-6-chloro-3a,4,9,9a-tetrahydro-4-phenyl-benz[f]isoindoline, M.P. 115°–117°;

(9aRS)-2-benzyl-9,9a-dihydro-6-methyl-4-phenyl-benz[f]isoindoline, M.P. 139°–143°;

(9aRS)-9,9a-dihydro-2-methyl-4-phenyl-benz[f]isoindoline, M.P. of the hydrogen maleate salt form 158°–162° (decomp.);

(9aRS)-2-benzyl-9,9a-dihydro-7-methyl-4-phenyl-benz[f]isoindoline, M.P. 139°–142°;

(9aRS)-2-benzyl-9,9a-dihydro-4-phenyl-benz[f]isoindoline, M.P. 113°–115°;

(9aRS)-2-benzyl-6-chloro-9,9a-dihydro-4-phenyl-benz[f]isoindoline, M.P. 266°–268°.

Examples 6, 9, 10, 11, 12, 13 and 20 illustrate processes for the production of the required starting materials.

The following Examples illustrate further process variants in accordance with process (a):

EXAMPLE 2

(3aRS,4SR,9aSR)-4-(3a,4,9,9a-tetrahydro-4-phenyl-benz[f]isoindolin-2-yl)-2-butanone [variant of process (a)]

A solution of 7.4 g of (3aRS,4SR,9aSR)-3a,4,9,9a-tetrahydro-4-phenyl-benz[f]isoindoline in 60 cc of ethanol is heated to the boil at reflux for 1½ hours after the addition of 3 cc of methylvinylketone, and is subsequently concentrated by evaporation. The residue is chromatographed on silica gel with ethyl acetate. After concentrating by evaporation, the filtrate yields the title compound as oily residue. Hydrogen maleate salt form: M.P. 121°–124° (after crystallization from ethanol).

EXAMPLE 3

(3aRS,4SR,9aSR)-3a,4,9,9a-tetrahydro-4-phenyl-benz[f]isoindoline-2-propionic acid methyl ester [variant of process (a)]

A mixture of 15 g of (3aRS,4SR,9aSR)-3a,4,9,9a-tetrahydro-4-phenyl-benz[f]isoindoline, 5.9 g of acrylic acid methyl ester and 1 cc of a 40% solution of benzyl trimethyl ammonium hydroxide in methanol is stirred at 50° for 4 hours and is then concentrated by evaporation. The evaporation residue is reduced to a slime with silica gel in benzene/ethyl acetate (9:1) and filtration is effected. Upon concentrating the filtrate by evaporation, the title compound, having a M.P. of 75°–76° (after crystallization from ether/petroleum ether), is obtained.

EXAMPLE 4

(3aRS,4SR,9aSR)-3a,4,9,9a-tetrahydro-4-phenyl-benz[f]isoindoline-2-propionic acid [hydrolysis ester—process (h)]

10 g of (3aRS,4SR,9aSR)-3a,4,9,9a-tetrahydro-4-phenyl-benz[f]isoindoline-2-propionic acid methyl ester are heated to the boil at reflux in 50 cc of 2 N hydrochloric acid for 5 hours. The solution is then concentrated by evaporation, the residue is dissolved in water, the pH of the solution is adjusted to 1 with caustic soda solution, and 1 equivalent of 1,5-naphthalene disulphonic acid is added, whereby the bis-1,5-naphthalene-disulphonate salt form of the title compound is obtained in sticky form. The supernatant water is poured off and the resin is triturated with acetone, whereby it crystallizes. M.P. 193°–195°.

EXAMPLE 5

(3aRS,4SR,9aSR)-2-(2-hydroxyethyl)-3a,4,9,9a-tetrahydro-6-methyl-4-(p-tolyl)-2-benz[f]isoindoline [variant of process (a)]

1.3 g of ethylene oxide are passed, with stirring, at −15°, through a solution of 4 g of (3aRS,4SR,9aSR)-3a,4,9,9a-tetrahydro-6-methyl-4-(p-tolyl)benz[f]isoindoline in 30 cc of ethanol. The mixture is allowed to stand at +5° for 16 hours and is then concentrated. The residue is chromatographed on 30 g of silica gel with methylene chloride/methanol/aqueous saturated ammonia (95:4.5:0.5), whereby the title compound, having a M.P. of 128°–129° (after crystallization from methylene chloride/petroleum ether), is obtained.

The compounds described in Examples 2 to 5 may also be produced in a manner analogous to Example 1.

Produced in a manner analogous to Example 2:
4-[(9aRS)-9,9a-dihydro-4-phenyl-benz[f]isoindolin-2-yl]butan-2-one, M.P. of the hydrogen maleate salt form 132°–134°.

Produced in a manner analogous to Examples 3 and 4:
[(9aRS)-9,9a-dihydro-4-phenyl-benz[f]isoindolin-2-yl]propionic acid, M.P. of the bis(base)naphthalene-1,5-disulphonate 206°–210°.

EXAMPLE 6

(3aRS,4SR,9aSR)-3a,4,9,9a-tetrahydro-4-phenyl-benz[f]isoindoline [process (a')]

22.3 g of (3aRS,4SR,9aSR)-3a,4,9,9a-tetrahydro-4-phenyl-benz[f]isoindoline-2-trifluoroacetamide are dissolved in a 3 N caustic potash solution in methanol with heating. The mixture is stirred at room temperature for 30 minutes, is subsequently poured on water and extracted with methylene chloride. The extract is dried over sodium sulphate, the solution is concentrated by evaporation and the residue is crystallized from methylene chloride/pentane, whereby the title compound, having a M.P. of 136°–138°, is obtained.

The (3aRS,4SR,9aSR)-3a,4,9,9a-tetrahydro-4-phenyl-benz[f]isoindoline-2-trifluoroacetamide, required as starting material, may, for example, be obtained as follows:

A solution of 310 g of N,N-bis-(trans-cinnamyl)trifluoroacetamide in 6 liters of o-dichlorobenzene is heated to the boil at reflux for 16 hours in an atmosphere of argon and is subsequently concentrated by evaporation. The residue is crystallized from methylene chloride/pentane, whereby (3aRS,4SR,9aSR)-3a,4,9,9a-tetrahydro-4-phenyl-benz[f]isoindoline-2-trifluoroacetamide, having a M.P. of 150°–153°, is obtained.

IR (CH$_2$Cl$_2$) 1690, no band at 950 to 990 cm$^{-1}$.

The N,N-bis-(trans-cinnamyl)trifluoroacetamide, required as starting material, may be produced as follows:

A solution of 275 g of N-cinnamyl-trifluoroacetamide in 600 cc of hexamethyl phosphoric acid triamide is added dropwise, while cooling and stirring, to a suspension of 30.2 g of sodium hydride in 540 cc of hexamethyl phosphoric acid triamide. After gas evolution is complete, a solution of 248.5 g of cinnamyl bromide in 540 cc of hexamethyl phosphoric acid triamide is added dropwise, and the mixture is stirred at 25° for 16 hours. The reaction mixture is then poured on water and extracted with ether. The ether solution, which has been dried over sodium sulphate, is concentrated by evaporation, and the oily residue is chromatographed with toluene on 1.5 kg of silica gel.

Upon concentrating by evaporation, the filtrate yields N,N-bis-(trans-cinnamyl)trifluoroacetamide as oily residue.

IR (CH$_2$Cl$_2$) 1690, 968 cm$^{-1}$.

The title compound may also be obtained under the usual conditions by reduction of (3aRS,4SR,9aSR)-3a,4,9,9a-tetrahydro-4-phenyl-benz[f]isoindoline-2-p-toluenesulphonic acid amide. The (3aRS,4SR,9aSR)-3a,4,9,9a-tetrahydro-4-tetrahydro-4-phenyl-benz[f]isoindoline-2-p-toluenesulphonic acid amide, required as starting material, may, for example, be obtained as follows:

A solution of 2 g of N,N-bis-(trans-cinnamyl)-p-toluenesulphonic acid amide in 120 cc of o-dichlorobenzene is heated to the boil at reflux for 48 hours in an atmosphere of argon and is subsequently concentrated by evaporation, whereby (3aRS,4SR,9aSR)-3a,4,9,9a-tetrahydro-4-phenyl-benz[f]isoindoline-2-p-toluenesulphonic acid amide is obtained as residue. M.P. 185°–187° (after crystallization from ether/pentane).

The following compounds of formula Ib may be obtained in a manner analogous to that described in Example 6, using the corresponding starting materials and process (a'):

(3aRS,4SR,9aSR)-6-chloro-4-(4-chlorophenyl)-3a,4,9,9a-tetrahydro-benz[f]isoindoline, M.P. 133°–134°;

(3aRS,4SR,9aSR)-6-fluoro-4-(p-fluorophenyl)-3a,4,9,9a-tetrahydro-benz[f]isoindoline, M.P. of the hydrogen maleate salt form 134°–136°;

(3aRS,4SR,9aSR)-7-chloro-4-(m-chlorophenyl)-3a,4,9,9a-tetrahydro-benz[f]isoindoline, M.P. of the hydrogen maleate salt form 166°–168°;

(3aRS,4SR,9aSR)-3a,4,9,9a-tetrahydro-6-methyl-4-(p-tolyl)benz[f]isoindoline, M.P. 129°–132°;

(3aRS,4SR,9aSR)-3a,4,9,9a-tetrahydro-6-methyl-4-phenyl-benz[f]isoindoline, M.P. of the hydrochloride salt form 255°–262° C.;

(3aRS,4SR,9aSR)-3a,4,9,9a-tetrahydro-7-methyl-4-phenyl-benz[f]isoindoline, M.P. of the hydrochloride salt form 225°–227°;

(3aRS,4SR,9aSR)-6-chloro-3a,4,9,9a-tetrahydro-4-phenyl-benz[f]isoindoline, M.P. of the hydrochloride salt form 205°–207°;

(3aRS,4RS,9aSR)-3a,4,9,9a-tetrahydro-4-phenyl-benz[f]isoindoline, M.P. of the hydrochloride salt form 256°–258°;

(3aRS,4RS,9aSR)-3a,4,9,9a-tetrahydro-6-methyl-4-phenyl-benz[f]isoindoline, M.P. of the hydrochloride salt form 215°–220°;

(3aRS,4RS,9aSR)-3a,4,9,9a-tetrahydro-7-methyl-4-phenyl-benz[f]isoindoline, M.P. of the hydrochloride salt form 226°–230°;

(3aRS,4RS,9aSR)-6-chloro-3a,4,9,9a-tetrahydro-4-phenyl-benz[f]isoindoline, M.P. 144°–145°;

(9aRS)-9,9a-dihydro-4-phenyl-benz[f]isoindoline, M.P. of the hydrochloride salt form 238°–243° (decomp.).

EXAMPLE 7

(3aRS,4SR,9aSR)-3a,4,9,9a-tetrahydro-2-methyl-4-phenyl-benz[f]isoindoline [process (b)]

A mixture of 8 g of (3aRS,4SR,9aSR)-3a,4,5,9,9a-tetrahydro-4-phenyl-benz[f]isoindoline, 120 cc of a 40% aqueous solution of formaldehyde and 320 cc of methanol is stirred in an atmosphere of hydrogen after the addition of a catalytic amount of Raney nickel, until the take up of gas is complete. The filtered reaction mixture is then concentrated by evaporation, methanol is added to the residue, the insoluble material is filtered off and the solution is concentrated by evaporation, whereby the title compound is obtained as residue. The hydrochloride salt form of the title compound has a M.P. of 207°–209° (ethanol/ether).

EXAMPLE 8

(3aRS,4SR,9aSR)-6-chloro-4-(p-chlorophenyl)-3a,4,9,9a-tetrahydro-2-methyl-benz[f]isoindoline [process (b)]

A mixture of 1.5 g of (3aRS,4SR,9aSR)-6-chloro-4-(p-chlorophenyl)-3a,4,9,9a-tetrahydro-benz[f]isoindoline, 10 cc of 100% formic acid and 10 cc of a 40% aqueous formaldehyde solution is heated to the boil at reflux for 2 hours in an atmosphere of nitrogen. The mixture is concentrated by evaporation, the residue is taken up in water, the solution is made alkaline with concentrated caustic soda solution and is extracted with methylene chloride. Ether is added to the dried extracts until they are turbid, filtration through Hyflo and concentration by evaporation are effected, whereby the title compound is obtained as residue. M.P. 133°–135° (after crystallization from ether).

The following compounds are obtained in a manner analogous to that described in Examples 7 and 8 from the corresponding starting materials and using process (b):

(3aRS,4SR,9aSR)-3a,4,9,9a-tetrahydro-2-isopropyl-4-phenyl-benz[f]isoindoline, M.P. of the bis(base) naphthalene-maleate salt form 150–195°–;

(3aRS,4SR,9aSR)-3a,4,9,9a-tetrahydro-2,6-dimethyl-4-(p-tolyl)benz[f]isoindoline, M.P. of the bis(base)-naphthalene-1,5-disulphonate salt form 195–198°;

(3aRS,4SR,9aSR)-3a,4,9,9a-tetrahydro-2,6-dimethyl-4-phenyl-benz[f]isoindoline, M.P. of the bis(base) naphthalene-1,5-disulphonate salt form 280°–283°;

(3aRS,4SR,9aSR)-3a,4,9,9a-tetrahydro-2,7-dimethyl-4-phenyl-benz[f]isoindoline, M.P. of the bis(base) naphthalene-1,5-disulphonate salt form 244°–248°;

(3aRS,4RS,9aSR)-3a,4,9,9a-tetrahydro-2,6-dimethyl-4-phenyl-benz[f]isoindoline, M.P. of the bis(base) naphthalene-1,5-disulphonate salt form 183°–187°;

(3aRS,4RS,9aSR)-3a,4,9,9a-tetrahydro-2,7-dimethyl-4-phenyl-benz[f]isoindoline, M.P. of the bis(base) naphthalene-1,5-disulphonate salt form 204°–207°;

(3aRS,4RS,9aSR)-3a,4,9,9a-tetrahydro-2-methyl-4-phenyl-benz[f]-isoindoline, M.P. of the bis(base)naphthalene-1,5-disulphonate salt form 297°–303°.

The following compounds are obtained in a manner analogous to that described in Example 8 from the corresponding starting materials and using process (b):

(3aRS,4SR,9aSR)-7-chloro-4-(m-chlorophenyl)-3a,4,9,9a-tetrahydro-2-methyl-benz[f]isoindoline, M.P. of the bis(base)naphthalene-1,5-disulphonate salt form 244°–248°;

(3aRS,4SR,9aSR)-6-chloro-3a,4,9,9a-tetrahydro-2-methyl-4-phenyl-benz[f]isoindoline, M.P. of the hydrochloride salt form 231°–233°;

(3aRS,4SR,9aSR)-2-ethyl-6-chloro-3a,4,9,9a-tetrahydro-4-phenyl-benz[f]isoindoline (3aRS,4SR,9aSR)-2n-butyl-6-chloro-3a,4,9,9a-tetrahydro-4-phenyl-benz[f]isoindoline (3aRS,4SR,9aSR)-6-chloro-2isopropyl-3a,4,9,9a-tetrahydro-4-phenyl-benz[f]isoindoline (9aRS)-9,9a-dihydro-2-methyl-4-phenyl-benz[f]isoindoline, M.P. of the hydrogen maleate salt form 158°–162° (decomp.)

EXAMPLE 9

(3aRS,4SR,9aSR)-3a,4,9,9a-tetrahydro-6-methyl-4-phenyl-benz[f]isoindoline [process c,b']

A solution of 20.2 g of (3aRS,4RS,9aSR)-3a,4,9,9a-tetrahydro-6-methyl-4-phenyl-benz[f]isoindoline in 500 cc of n-butanol saturated with solid potassium hydroxide is heated to the boil at reflux for 70 hours in an atmosphere of argon, and is subsequently concentrated by evaporation. The residue is divided between water/methylene chloride, the organic phase is dried and concentrated by evaporation, the residue is taken up in an excess of hydrochloride acid in methanol, the solution is concentrated by evaporation, and after crystallization of the residue from methanol/ether, the hydrochloride salt form of the title compound, having a M.P. of 174°–176° (decomp.), is obtained.

EXAMPLE 10

(3aRS,4SR,9aSR)-6-chloro-3a,4,9,9a-tetrahydro-4-phenyl-benz[f]isoindoline [process (b')]

6.4 g of (3aRS,4RS,9aSR)-6-chloro-3a,4,9,9a-tetrahydro-2-phenoxycarbonyl-4-phenyl-benz[f]-isoindoline are heated to the boil at reflux in 320 cc of a saturated solution of potassium hydroxide in n-butanol for 70 hours in an atmosphere of nitrogen. The reaction mixture is then concentrated, the residue is taken up in water and extraction is effected with methylene chloride. The washed and dried methylene chloride solution is concentrated by evaporation, whereby the title compound is obtained. M.P. of the hydrochloride salt form 205°–207° (after crystallization from methylene chloride/ether).

The following compounds are obtained in a manner analogous to that described in Example 9 or 10 from the corresponding starting materials and using process (b'):

(3aRS,4SR,9aSR)-3a,4,9,9a-tetrahydro-4-phenyl-benz[f]-isoindoline, M.P. 136°–138°;

(3aRS,4SR,9aSR)-6-chloro-4-(4-chlorophenyl)-3a,4,9,9a-tetrahydro-benz[f]isoindoline, M.P. 133°–134°;

(3aRS,4SR,9aSR)-6-fluoro-4-(p-fluorophenyl)-3a,4,9,9a-tetrahydro-benz[f]isoindoline, M.P. of the hydrogen maleate salt form 134°–136°;

(3aRS,4SR,9aSR)-7-chloro-4-(m-chlorophenyl)-3a,4,9,9a-tetrahydro-benz[f]isoindoline, M.P. of the hydrogen maleate salt form 166°–168°;

(3aRS,4SR,9aSR)-3a,4,9,9a-tetrahydro-6-methyl-4-(p-tolyl)benz[f]isoindoline, M.P. 129°–132°; 225°–

(3aRS,4SR,9aSR)-3a,4,9,9a-tetrahydro-7-methyl-4-phenyl-benz[f]isoindoline, M.P. of the hydrochloride salt form 225°–227°.

The following compounds are obtained in a manner analogous to that described in Example 9 from the corresponding starting materials and using process (c):

(3aRS,4SR,9aSR)-3a,4,9,9a-tetrahydro-2-methyl-4-phenyl-benz[f]isoindoline, M.P. of the hydrochloride salt form 207°–209°;

(3aRS,4SR,9aSR)-2-cyclopropylmethyl-3a,4,9,9a-tetrahydro-4-phenyl-benz[f]isoindoline, M.P. 65°–68°;

(3aRS,4SR,9aSR)-3a,4,9,9a-tetrahydro-2-isopropyl-4-phenyl-benz[f]isoindoline, M.P. of the hydrogen maleate salt form 150°–158°;

(3aRS,4SR,9aSR)-2-(o-chlorophenethyl)-3a,4,9,9a-tetrahydro-4-phenyl-benz[]isoindoline, M.P. of the hydrogen maleate salt form 178°–179°;

(3aRS,4SR,9aSR)-2-(3a,4,9,9a-tetrahydro -4-phenyl-benz[f]-isoindolin-2-yl)acetophenone, M.P. 120°–130°;

(3aRS,4SR,9aSR)-p-fluoro-4-(3a,4,9,9a-tetrahydro-4-phenyl-benz[f]isoindolin-2-yl)butyrophenone, M.P. 81°–84°;

(3aRS,4SR,9aSR)-6-chloro-4-(4-chlorophenyl)-3a,4,9,9a-tetrahydro-2-methyl-benz[f]isoindoline, M.P. 133°–135°;

(3aRS,4SR,9aSR)-6-chloro-4-(4-chlorophenyl)-2-cyclopropylmethyl-3a,4,9,9a-tetrahydro-benz[f]isoindoline, M.P. 124°–126°;

(3aRS,4SR,9aSR)-7-chloro-4-(m-chlorophenyl)-3a,4,9,9a-tetrahydro-2-methyl-benz[f]isoindoline, M.P. of the bis(base)napthalene-1,5-disulphonate salt form 244°–248°;

(3aRS,4SR,9aSR)-7-chloro-4-(m-chlorophenyl)-2cyclopropylmethyl-3a,4,9,9a-tetrahydro-benz[f]isoindoline, M.P. of the bis(base) naphthalene-1,5-disulphonate salt form 243°–247°;

(3aRS,4SR,9aSR)-3a,4,9,9a-tetrahydro-2,6-dimethyl-4-(p-tolyl)benz[f]isoindoline, M.P. of the bis(base)-naphthalene-1,5-disulphonate salt form (195°–198°;

(3aRS,4SR,9aSR)-2-cyclopropylmethyl-3a,4,9,9a-tetrahydro-6-methyl-4-(p-tolyl)benz[f]isoindoline, M.P. 98°–100°;

(3aRS,4SR,9aSR)-2-hydroxyethyl)-3a,4,9,9a-tetrahydro-6-methyl-4-(p-tolyl)-2-benz[f]isoindoline, M.P. 128°–129°;

(3aRS,4SR,9aSR)-3a,4,9,9a-tetrahydro-2,6-dimethyl-4-phenyl-benz[f]isoindoline, M.P. of the bis(base)-naphthalene-1,5-disulphonate 280°–283°;

(3aRS,4SR,9aSR)-6-chloro-2-cyclopropylmethyl-3a,4,9,9a-tetrahydro-4-phenyl-benz[f]isoindoline (3aRS,4SR,9aSR)-2-ethyl-6-chloro-3a,4,9,9a-tetrahydro-4-phenyl-benz[f]isoindoline (3aRS,4SR,9aSR)-2-n-butyl-6-chloro-3a,4,9,9a-tetrahydro-4-phenyl-benz[f]isoindoline (3aRS,4SR,9aSR)-6-chloro-2-isopropyl-3a,4,9,9a-tetrahydro-4-phenyl-benz[f]isoindoline (3RS,4SR,9aSR)-2-cyclopropylmethyl-3a,4,9,9a-tetrahydro-6-methyl-4-phenyl-benz[f]isoindoline, M.P. of the hydrochloride salt form 198°–204°;

(3aRS,4SR,9aSR)-3a,4,9,9a-tetrahydro-2,7-dimethyl-4-phenyl-benz[f]isoindoline, M.P. of the bis(base) naphthalene-1,5-disulphonate salt form 244°–248°;

(3aRS,4SR,9aSR)-2-cyclopropylmethyl-3a,4,9,9a-tetrahydro-7-methyl-4-phenyl-benz[f]isoindoline, M.P. 79°–82°;

2-[(3aRS,4SR,9aSR)-3a,4,9,9a-tetrahydro-7-methyl-4-phenyl-benz[f]isoindolin-2-yl]-p-fluoroacetophenone, M.P. of the hydrogen maleate salt form 164°–166°;

(3aRS,4SR,9aSR)-6-chloro-3a,4,9,9a-tetrahydro-2-methyl-4-phenyl-benz[f]isoindoline, M.P. of the hydrochloride salt form 231°–233°;

(3aRS,4SR,9aSR)-3a,4,9,9a-tetrahydro-2-(p-methylbenzyl)-4-phenyl-benz[f]isoindoline, M.P. 120°–121°;

(3aRS,4SR,9aSR)-3a,4,9,9a-tetrahydro-2-(p-methoxybenzyl)-4-phenyl-benz[f]isoindoline, M.P. 95°–100°.

EXAMPLE 11

(3aRS,4RS,9aSR)-3a,4,9,9a-tetrahydro-6-methyl-4-phenyl-benz[f]isoindoline [processes (e), (c$^j$)]

A solution of 0.55 g of palladium-II-chloride and 0.39 g of common salt in 50 cc of water is added at 25° to a solution of 35.2 g of (9aRS)-2-benzyl-9,9a-dihydro-6-methyl-4-phenyl-benz[f]isoindoline in 300 cc of ethanol. A solution of 2.0 g of sodium borohydride in 25 cc of water is added dropwise to the mixture at 0°, stirring is effected at 25° for 30 minutes, the pH of the solution is adjusted to 2 with aqueous concentrated hydrochloric acid, and hydrogenation is finally effected at 60° and a pressure of 4 atmospheres for 18 hours. The reaction mixture is filtered, the filtrate is concentrated, the residue is extracted with hot ethanol, and the clear solution is allowed to cool, whereby the hydrochloride salt form of the title compound, having a M.P. of 215°–220° (from methanol/ether), crystallizes.

EXAMPLE 12

(3aRS,4RS,9aSR)-2-benzyl-6-chloro-3a,4,9,9a-tetrahydro-4-phenyl-benz[f]isoindoline [processes (d), (c$^j$)]

190 cc of 57% hydriodic acid are added dropwise to a suspension of 30 g of (9aRS)-2-benzyl-6-chloro-9,9a-dihydro-4-phenyl-benz[f]isoindoline and 46.8 g of red phosphorus in 400 cc of glacial acetic acid, the mixture is subsequently heated to 110° for 5 ½ hours, is then poured on ice and made alkaline with caustic soda solution. After extraction with ethyl acetate, the organic phase is filtered through Celite, the filtrate is dried and concentrated by evaporation, whereby the title compound, having a M.P. of 115–117° (after crystallization from pentane), is obtained.

The following compounds are obtained in a manner analogous to that described in Examples 11 and 12 from the corresponding starting materials and using process (d) or (e):

(3aRS,4RS,9aSR)-3a,4,9,9a-tetrahydro-2,6-dimethyl-4-phenyl-benz[f]isoindoline, M.P. of the bis(base)-naphthalene-1,5-disulphonate salt form 183°–187°;

(3aRS,4RS,9aSR)-3a,4,9,9a-tetrahydro-2,7-dimethyl-4-phenyl-benz[f]isoindoline, M.P. of the bis(base)-naphthalene-1,5-disulphonate 204°–207°;

(3aRS,4RS,9aSR)-3a,4,9,9a-tetrahydro-2-methyl-4-phenyl-benz[f]isoindoline, M.P. of the bis(base)naphthalene-1,5-disulphonate 297°–303°.

The following compounds are obtained in a manner analogous to that described in Example 11, from the corresponding starting materials and using process (e) or (c$^j$):

(3aRS,4RS,9aSR)-3a,4,9,9a-tetrahydro-7-methyl-4-phenyl-benz[f]isoindoline, M.P. of the hydrochloride salt form 226°–230°;

(3aRS,4RS,9aSR)-3a,4,9,9a-tetrahydro-4-phenyl-benz[f]-isoindoline, M.P. of the hydrochloride salt form 256°–258°;

EXAMPLE 13

(3aRS,4RS,9aSR)-6-chloro-3a,4,9,9a-tetrahydro-4-phenyl-benz[f]isoindoline [process (a$^j$)]

A mixture of 8.8 g of (3aRS,4RS,9aSR)-6-chloro-3a,4,9,9a-tetrahydro-2-phenoxycarbonyl-4-phenyl-benz[f]isoindoline, 260 cc of methanol and 42 g of 50% caustic soda solution is heated to the boil at reflux for 15 hours in an atmosphere of nitrogen, is then concentrated and diluted with methylene chloride. The washed and dried organic phase is concentrated by evaporation, whereby the title compound, having a M.P. of 144°–145° (after crystallization from ether/penthane), is obtained.

The (3aRS,4RS,9aSR)-6-chloro-3a,4,9,9a-tetrahydro-2-phenoxycarbonyl-4-phenyl-benz[f]isoindoline, used as starting material, may be produced as follows:

3.65 cc of chloroformic acid phenyl ester are added at 0° to a solution of 9 g of (3aRS,4RS,9aSR)-2-benzyl-6-chloro-3a,4,9,9a-tetrahydro-4-phenyl-benz[f]-isoindoline in 90 cc of methylene chloride, stirring is effected at room temperature for 16 hours, washing is then effected with a 3 N caustic soda solution, 2 N hydrochloric acid and water, drying and concentration by evaporation are effected. The oily residue is chromatographed with toluene/ethyl acetate (1:1) on a 100-fold quantity of silica gel, whereby (3aRS,4RS,9aSR)-6-chloro-3a,4,9,9a-tetrahydro-2-phenoxycarbonyl-4-phenyl-benz[f]isoindoline, having a M.P. of 130–134° (after crystallization from ether), is obtained.

EXAMPLE 14

(9aRS)-2-benzyl-9,9a-dihydro-6-methyl-4-phenyl-benz[f]isoindoline [process f,d$^l$]

35 cc of 100% sulphuric acid are added dropwise to a solution of 27 g of lithium aluminium hydride in 400 cc of tetrahydrofuran at −5° while stirring in an atmosphere of nitrogen. The mixture is subsequently stirred at room temperature for 30 minutes, is again cooled to −5°, and a solution of 90 g of (9aRS)-2-benzyl-9,9a-dihydro-6-methyl-4-phenyl-benz[f]-isoindoline-1,3-dione in 1 liter of tetrahydrofuran is added dropwise within 30 minutes. After stirring at room temperature for 26 hours, the reaction mixture is decomposed by the addition of water and a 12% caustic soda solution, and the resulting precipitate is filtered off. The filtrate is concentrated by evaporation, the residue is taken up in methylene chloride, the filtered solution is concentrated and the residue is crystallized from ether/pentane, whereby the title compound, having a M.P. of 139°–143°, is obtained.

The (9aRS)-2-benzyl-9,9a-dihydro-6-methyl-4-phenyl-benz[f]isoindoline-1,3-dione, used as starting material, may be produced as follows:

A solution of 35 g of 2,5-dimethylbenzophenone and 31.5 g of N-benzylmaleimide in 500 cc of acetone or methylene chloride is irradiated with a mercury high pressure lamp through a pyrex filter, until all the material has reacted (20 to 130 hours), filtration and concentration by evaporation are then effected. After crystallization from ether, the residue yields 35 g of 2-benzyl-3a,4,9,9a-tetrahydro-6-methyl-4-phenyl-benz[f]isoindolin-4-ol-1,3-dione, having a M.P. of 162–164°, which are dissolved in 170 cc of trifluoroacetic acid. The solution is stirred at 25° for 3 hours and concentrated by evaporation. After crystallization from methylene chloride/methanol, the residue yields 30 g of (9aRS)-2-benzyl-9,9a-dihydro-6-methyl-4-phenyl-benz[f]isoindoline-1,3-dione, having a M.P. of 156°–158°.

The following compounds are obtained in a manner analogous to that described in Example 14, from the corresponding starting materials and using process (f) or (d$^l$):

(9aRS)-2-benzyl-9,9a-dihydro-7-methyl-4-phenyl-benz[f]-isoindoline, M.P. 139°–142°;
(9aRS)-2-benzyl-6-chloro-9,9a-dihydro-4-phenyl-benz[f]-isoindoline, M.P. 266°–268°;
(9aRS)-2-benzyl-9,9a-dihydro-4-phenyl-benz[f]isoindoline, M.P. 113°–115°;
(9aRS)-9,9a-dihydro-4-phenyl-benz[f]isoindoline, M.P. of the hydrochloride salt form 238°–243° (decomp.);
(9aRS)-9,9a-dihydro-2-methyl-4-phenyl-benz[f]isoindoline, M.P. of the hydrogen maleate salt form 158°–162° (decomp.).

EXAMPLE 15

(3aRS,4SR,9aSR)-2-cyclopropylmethyl-3a,4,9,9a-tetrahydro-4-phenyl-benz[f]-isoindoline [process (g)]

4.7 of cyclopropylcarboxylic acid chloride are added dropwise at −5° to a mixture of 7.5 g of (3aRS,4SR,9aSR)-3a,4,9,9a-tetrahydro-4-phenyl-benz[f]-isoindoline, 7.9 g of pyridine and 100 cc of methylene chloride. The mixture is stirred at room temperature for 1 hour, is then successively shaken with a 10% aqueous citric acid solution and a sodium hydrogen carbonate solution, is dried over sodium sulphate and concentrated by evaporation, whereby (3aRS,4SR,9aSR)-3a,4,9,9a-tetrahydro-4-phenyl-benz[f]isoindoline-2-cyclopropylcarboxylic acid amide, having a M.P. of 149°–151° (after crystallization from ether), is obtained as residue.

1 g of lithium aluminium hydride is added portionwise to a warm solution of 8.6 g of (3aRS,4SR,9aSR)-3a,4,9,9a-tetrahydro-4-phenyl-benz[f]-isoindoline-2-cyclopropylcarboxylic acid amide in 100 cc of tetrahydrofuran. The mixture is stirred at room temperature for 1 hour, is then decomposed with a 2 N caustic soda solution and filtered. The concentrated filtrate is reduced to a paste with silica gel in benzene/ethyl acetate (1:1), filtration and concentration by evaporation are effected, whereby the title compound, having a M.P. of 65–68° (after crystallization from pentane), is obtained.

The following compounds of formula Im are obtained in a manner analogous to that described in Example 15 from the corresponding starting materials and using process (g):

(3aRS,4SR,9aSR)-3a,4,9,9a-tetrahydro-2-methyl-4-phenyl-benz[f]isoindoline, M.P. of the hydrochloride salt form 207–209°;

(3aRS,4SR,9aSR)-6-chloro-2-cyclopropylmethyl-3a,4,9,9a-tetrahydro-4-phenyl-benz[f]isoindoline;

(3aRS,4SR,9aSR)-2-(o-chlorophenethyl)-3a,4,9,9a-tetrahydro-4-phenyl-benz[f]isoindoline, M.P. of the hydrogen maleate salt form 178–179°;

(3aRS,4SR,9aSR)-6-chloro-4-(4-chlorophenyl)-3a,4,9,9a-tetrahydro-2-methyl-benz[f]isoindoline, M.P. 133–135°;

(3aRS,4SR,9aSR)-6-chloro-4-(4-chlorophenyl)-2-cyclopropylmethyl-3a,4,9,9a-tetrahydro-benz[f]isoindoline, M.P. 124–126°;

(3aRS,4SR,9aSR)-7-chloro-4-(m-chlorophenyl)-3a,4,9,9a-tetrahydro-2-methyl-benz[f]isoindoline, M.P. of the bis(base)naphthalene-1,5-disulphonate 244–248°;

(3aRS,4SR,9aSR)-7-chloro-4-(m-chlorophenyl)-2-cyclopropylmethyl-3a,4,9,9a-tetrahydro-benz[f]isoindoline, M.P. of the bis(base)naphthalene-1,5-disulphonate salt form 243–247°;

(3aRS,4SR,9aSR)-3a,4,9,9a-tetrahydro-2,6-dimethyl-4-(p-tolyl)benz[f]isoindoline, M.P. of the bis(base) naphthalene-1,5-disulphonate salt form 195–198°;

(3aRS,4SR,9aSR)-2-cyclopropylmethyl-3a,4,9,9a-tetrahydro-6-methyl-4-(p-tolyl)benz[f]isoindoline, M.P. 98–100°;

(3aRS,4SR,9aSR)-2-(2-hydroxyethyl)-3a,4,9,9a-tetrahydro-6-methyl-4-(p-tolyl)-2-benz[f]isoindline, M.P. 128–129°;

(3aRS,4SR,9aSR)-3a,4,9,9a-tetrahydro-2,6-dimethyl-4-phenyl-benz[f]isoindoline, M.P. of the bis(base) naphthalene-1,5-disulfonate 280–283°;

(3aRS,4SR,9aSR)-2-cyclopropylmethyl-3a,4,9,9a-tetrahydro-6-methyl-4-phenyl-benz[f]isoindoline, M.P. of the hydrochloride salt form 198–204°;

(3aRS,4SR,9aSR)-3a,4,9,9a-tetrahydro-2,7-dimethyl-4-phenyl-benz[f]isoindoline, M.P. of the bis(base) naphthalene-1,5-disulphonate 244–248°;

(3aRS,4SR,9aSR)-2-cyclopropylmethyl-3a,4,9,9a-tetrahydro-7-methyl-benz[f]isoindoline, M.P. 79–82°;

(3aRS,4SR,9aSR)-2-ethyl-6-chloro-3a,4,9,9a-tetrahydro-4-phenyl-benz[f]isoindoline (3aRS,4SR,9aSR)-2-n-butyl-6-chloro-3a,4,9,9a-tetrahydro-4-phenyl-benz[f]isoindoline (3a RS,4SR,9aSR)-6-chloro-3a,4,9,9a-tetrahydro-2-methyl-4-phenyl-benz[f]isoindoline, M.P. of the hydrochloride salt form 231–233°;

(3aRS,4SR,9aSR)-3a,4,9,9a-tetrahydro-2-(p-methylbenzyl)-4-phenyl-benz[f]isoindoline, M.P. 120–121°;

(3aRS,4SR,9aSR)-3a,4,9,9a-tetrahydro-2-(p-methoxybenzyl)-4-phenyl-benz[f]isoindoline, M.P. 95–100°;

(3aRS,4RS,9aSR)-3a,4,9,9a-tetrahydro-2-methyl-4-phenyl-benz[f]isoindoline, M.P. of the bis(base)naphthalene-1,5-disulphonate salt form 297–303°;

(3aRS,4RS,9aSR) -3a,4,9,9a-tetrahydro-2,6-dimethyl-4-phenyl-benz[f]isoindoline, M.P. of the bis(base) naphthalene-1,5-disulphonate 183–187°;

(3aRS,4RS,9aSR)-3a,4,9,9a-tetrahydro-2,7-dimethyl-4-phenyl-benz[f]isoindoline, M.P. of the bis(base) naphthalene-1,5-disulphonate 204°–207°;

(3aRS,4RS,9aSR)-2-benzyl-6-chloro-3a,4,9,9a-tetrahydro-4-phenyl-benz[f]isoindoline, M.P. 115–117°;

(9aRS)-9,9a-dihydro-2-methyl-4-phenyl-benz[f]isoindoline, M.P. of the hydrogen maleate salt form 158–162° (decomp.);

(9aRS)-2-benzyl-9,9a-dihydro-4-dihydro-4-phenyl-benz[f]isoindoline, M.P. 265–269°;

(9aRS)-2-benzyl-9,9a-dihydro-6-methyl-4-phenyl-benz[f]-isoindoline, M.P. 139–143°;

(9aRS)-2-benzyl-9,9a-dihydro-7-methyl-4-phenyl-benz[f]-isoindoline, M.P. 139–142°;

(9aRS)-2-benzyl-6-chloro-9,9a-dihydro-4-phenyl-benz[f]-isoindoline, M.P. of the hydrochloride salt form 266–268°.

The following are characteristic Examples which illustrate the described processes for the production of the required starting materials:

EXAMPLE 16

(3aRS,4SR,9aSR)-6-chloro-4-(p-chlorophenyl)-3a,4,9,9a-tetrahydro-benz[f]isoindoline-2-trifluoroacetamide A solution of 30 g of N,N-bis-(trans-p-chlorocinnamyl)trifluoroacetamide in 600 cc of o-dichlorobenzene is heated to the boil at reflux for 16 hours in an atmosphere of argon and is subsequently concentrated by evaporation. The residue is chromatographed on 250 g of silica gel with benzene. The filtrate is concentrated by evaporation, whereby the title compound is obtained as residue. M.P. 107–112° (after crystallization from ether/pentane).

The N,N-bis-(trans-p-chlorocinnamyl)-trifluoroacetamide, used as starting material, may be produced by alkylation of N-trans-p-chlorocinnamyltrifluoroacetamide with trans-p-chlorocinnamyl bromide (in a manner analogous to Example 6).

EXAMPLE 17

(3aRS,4SR,9aSR)-6-fluoro-4-(p-fluorophenyl)-3a-4,9,9a-tetrahydro-benz[f]isoindoline-2-trifluoroacetamide The title compound having a M.P. of 173–176° (after crystallization from ether), is produced in a manner analogous to that described in Example 6, by thermic cyclization of N,N-bis-(trans-p-fluorocinnamyl)-trifluoroacetamide.

The N,N-bis-(trans-p-fluorocinnamyl)-trifluoroacetamide, having a M.P. of 77–79° (after crystallization from chloroform), required as starting material, may be produced in a manner analogous to that described in Example 6 from N-p-fluorocinnamyl-tri-fluoroacetamide and p-fluorocinnamyl bromide.

EXAMPLE 18

(3aRS,4SR,9aSR)-7-chloro-4-(m-chlorophenyl)-3a,4,9,9a-tetrahydro-benz[f]isoindoline-2-trifluoroacetamide The title compound is obtained as an oil by thermic cyclization of N,N-bis-(trans-m-chlorocinnamyl)-trifluoroacetamide in a manner analogous to that described in Example 6 and is purified by chromatography on silica gel (benzene/ethyl acetate 19:1). The N,N-bis-(trans-m-chlorocinnamyl)trifluoroacetamide (oil), required as starting material, may be produced in a manner analogous to that described in Example 6 from N-m-chlorocinnamyl trifluoroacetamide and m-chlorocinnamyl bromide.

EXAMPLE 19

(3aRS,4SR,9aSR)-3a,4,9,9a-tetrahydro-6-methyl-4-(p-tolyl)benz[f]isoindoline-2-trifluoroacetamide The title compound, having a M.P. of 110–113° (after crystallization from ether/pentane), is obtained in a manner analogous to that described in Example 6, by thermic cyclization of N,N-bis-(trans-p-methylcinnamyl)trifluoroacetamide.

The N,N-bis-(trans-p-methylcinnamyl)-trifluoroacetamide (oil), required as starting material, may be produced in a manner analogous to that described in Example 6 from N-p-methylcinnamyl trifluoroacetamide and p-methylcinnamyl bromide.

EXAMPLE 20

(9aRS)-9,9a-dihydro-4-phenyl-benz[f]-isoindoline-2-trifluoroacetamide

A solution of 218 g of N-(trans-cinnamyl)-N-(3-phenyl-2-propinyl)trifluoroacetamide in 4.4 liters of o-dichlorobenzene is heated to the boil at reflux for 5 hours in an atmosphere of argon and is subsequently concentrated by evaporation. After crystallization from ether/pentane, the residue yields the title compound, having a M.P. of 195–197°.

The N-(trans-cinnamyl)-N-(3-phenyl-2-propinyl)trifluoroacetamide, used as starting material, may be produced by alkylation of N-(trans-cinnamyl)-trifluoroacetamide with 1-bromo-3-phenyl-2-propine.

In analogous manner to that disclosed in Example 1 the following (3aRS,4SR,9aSR) compounds of formula I are produced
wherein
$R_1$ is 7-Cl and
$R_2$ is 3-Cl and
R is . $CH_2$ . $C\!=\!C$ . $C_2H_5$     (a)

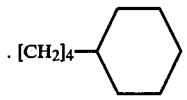  (b)

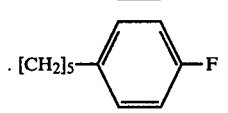  (c)

-continued

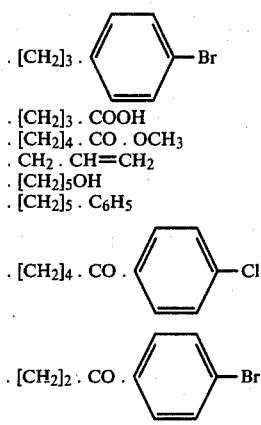

. [CH₂]₃ .  (d) (with Br-phenyl)
. [CH₂]₃ . COOH  (e)
. [CH₂]₄ . CO . OCH₃  (f)
. CH₂ . CH=CH₂  (g)
. [CH₂]₅OH  (h)
. [CH₂]₅ . C₆H₅  (i)
. [CH₂]₄ . CO . (phenyl-Cl)  (k)
. [CH₂]₂ . CO . (phenyl-Br)  (l)

and also the (3aRS,4SR,9aSR) compound wherein
  R₁ is 6-Br,
  R₂ is 4-Br and
  R is CH₃ from the corresponding R=H compound.
In analogous manner to that described in Example 1 there are prepared the following (3aRS,4SR,9aSR) compounds of formula I wherein, X and Y are both hydrogen and

| R₁ | R₂ | R | M.P. °C. |
|---|---|---|---|
| 6-CH₃ | H | . CH₂ . CH₂ . OH | 160°–163°¹ |
| 7-CH₃ | H | . CH₂ . CH₂ . OH | 217°–220°² |
| H | H | . CH₂ . CH₂ . OH | 227°–231°² |
| 6-CH₃ | 4-CH₃ | . CH₂ . C[CH₃]₂ . OH | 162°–5°³ |

¹HCL salt
²Bis[base]naphthalene-1,5-disulphonate
³Hydrogen maleate.

The following compounds are obtained in analogous manner to that described in Example I:
(3aRS,4SR,9aSR)-6-chloro-4-(p-chlorophenyl)-3a,4,9,9a-tetrahydro-2-methyl-benz[f]isoindoline.
(3aRS,4SR,9aSR)-6-chloro-4-(m-chlorophenyl)-3a,4,9,9a-tetrahydro-2-methyl-benz[f]isoindoline.
(3aRS,4SR,9aSR)-6-chloro-4-(o-chlorophenyl)-3a,4,9,9a-tetrahydro-2-methyl-benz[f]isoindoline.
(3aRS,4SR,9aSR)-6-chloro-3a,4,9,9a-tetrahydro-2-methyl-4-(o-tolyl)-benz[f]isoindoline.
(3aRS,4SR,9aSR)-6-chloro-3a,4,9,9a-tetrahydro-2-methyl-4-(m-tolyl)-benz[f]isoindoline.
(3aRS,4SR,9aSR)-6-chloro-3a,4,9,9a-tetrahydro-2-methyl-4-(p-tolyl)-benz[f]isoindoline.
(3aRS,4SR,9aSR)-4-(p-ethylphenyl)-6-chloro-3a,4,9,9a-tetrahydro-2-methyl-benz[f]isoindoline.
(3aRS,4SR,9aSR)-4-(p-bromophenyl)-6-chloro-3a,4,9,9a-tetrahydro-2-methyl-benz[f]isoindoline.
(3aRS,4SR,9aSR)-6-chloro-4-(p-fluorophenyl)-3a,4,9,9a-tetrahydro-2-methyl-benz[f]isoindoline.

The compounds of formula I have not been described in the literature.

The compounds of formula I are useful because they possess pharmacological activity in animals. In particular, the compounds of formula I are useful as antidepressant agents, as indicated in standard tests, for example by an inhibition of tetrabenazine-induced catalepsy in rats on p.o. administration of from 2 to 30 mg/kg animal body weight, of the compounds.

For the above-mentioned use the dosage will, of course, vary depending on the compound employed, mode of administration and therapy desired. However, in general, satisfactory results are obtained when administered at a daily dosage of from 1 mg to about 30 mg per kg animal body weight, conveniently given in divided doses 2 to 4 times a day or in sustained release form. For the larger mammal, the total daily dosage is in the range from about 50 to about 500 mg, and dosage forms suitable for oral administration comprise from about 12 mg to about 250 mg of the compounds admixed with a solid or liquid pharmaceutical carrier or diluent.

The compounds of formula I are furthermore useful as analgesic agents, as indicated in standard tests, for example in the tail-pinch test in mice on s.c. administration of from 15 to 50 mg/kg animal body weight, in the tail-flick test in mice on s.c. administration of from 30 to 100 mg/kg animal body weight, in the hot plate test in mice on p.o. administration of from 30 to 100 mg/kg animal body weight, and in the phenyl benzoquinone syndrome test in mice on p.o. administration of from 30 to 100 mg/kg animal body weight.

For this use the dosage will, of course, vary depending on the compound employed, mode of administration and treatment desired. However, in general, satisfactory results are obtained when administered at a daily dosage of from about 0.5 mg to about 100 mg per kg animal body weight, conveniently given in divided doses 2 to 4 times a day or in sustained release form. For the larger mammals, the total daily dosage is in the range from about 30 to 300 mg, and dosage forms suitable for oral administration comprise from about 7 mg to about 150 mg of the compounds admixed with a solid or liquid pharmaceutical carrier or diluent.

| EXAMPLE: Tablets | |
|---|---|
| (3aRS,4SR,9aSR)-3a,4,9,9a-tetrahydro-2-methyl-4-phenyl-benz[f]-isoindoline-hydrochloride* | 30 mg |
| magnesium stearate | 1 mg |
| polyvinyl pyrrolidone | 4 mg |
| talc | 5 mg |
| maize starch | 10 mg |
| lactose | 118 mg |
| dimethyl silicone oil | 0,5 mg |
| polyethylene glycol 6000 | 1,5 mg |
| | 170.- mg |

*corresponds with 26,3 mg base

The active compound is mixed in accordance with known methods with the above mentioned pharmacologically inert adjuvants and carriers, and the mixture is granulated and pressed into tablets by methods known per se.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

A class of compounds of formula I comprises compounds of formula Iw

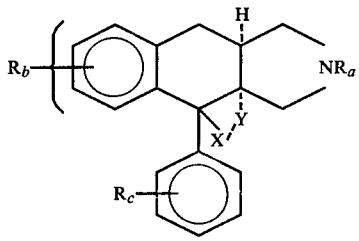

wherein
X and Y are as defined in claim 1,
$R_a$ is (i) hydrogen, (ii) alkyl of 1 to 3 carbon atoms, (iii) alkenyl or alkynyl of 3 to 5 carbon atoms, the multiple bond thereof being in other than the α-position thereof, (iv) cyclopropylmethyl, (v) hydroxyethyl, (vi) phenylalkyl of 7 or 8 carbon atoms in the aggregate thereof (vii), phenylalkyl of 7 or 8 carbon atoms in the aggregate thereof monosubstituted by fluorine, chlorine, methyl or methoxy, (viii) acetonyl, 3-oxobutyl, phenacyl, p-fluorphenacyl or 4-(p-fluorphenyl)-4-oxobutyl and $R_b$ and $R_c$ are identical or different and each is hydrogen, chlorine, fluorine or methyl.

The (3aRS,4SR,9aSR)-tetrahydrobenz[f]isoindolines of formula I, are especially interesting.

A class of preferred compounds comprises the compounds of formula

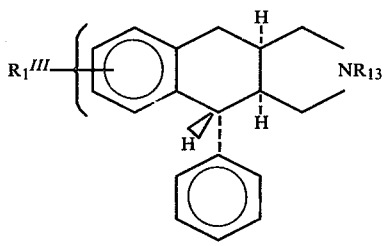

wherein
$R_1{}^{III}$ is hydrogen, methyl or chlorine, and
$R_{13}$ is methyl, 2-propinyl, cyclopropylmethyl or acetonyl,
or compounds of formula Iz

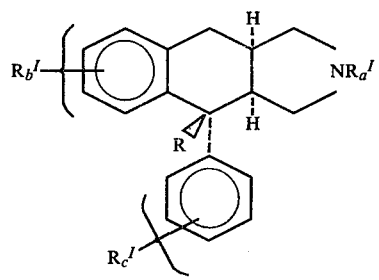

wherein
$R_a{}^I$ is hydrogen, methyl, 2-propinyl, cyclopropylmethyl, acetonyl and
$R_b{}^I$ and $R_c{}^I$ are independently hydrogen, methyl or chlorine.

We claim:
1. A compound of formula

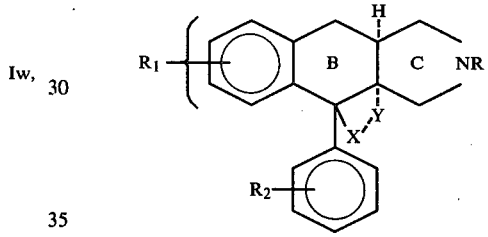

wherein
R is (i) hydrogen, (ii) alkyl of 1 to 5 carbon atoms, (iii) alkenyl or alkynyl of 3 to 5 carbon atoms, the multiple bond thereof being in other than the α-position, (iv) alkyl of 1 to 4 carbon atoms substituted by cycloalkyl of 3 to 6 carbon atoms, (v) hydroxyalkyl of 2 to 5 carbon atoms, (vi) phenylalkyl of 7 to 11 carbon atoms in the aggregate thereof, (vii) phenylalkyl of 7 to 11 carbon atoms in the aggregate thereof monosubstituted in the phenyl thereof by halogen, alkoxy of 1 to 4 carbon atoms or alkyl of 1 to 4 carbon atoms, or (viii) A—CO—$R_3$,
wherein
A is alkylene of 1 to 4 carbon atoms, and
$R_3$ is alkyl of 1 to 5 carbon atoms, alkoxy of 1 to 4 carbon atoms, hydroxy, phenyl or phenyl substituted by halogen,
$R_1$ and $R_2$ are identical or different and each is hydrogen, halogen or alkyl of 1 to 4 carbon atoms, and either (i) each of
X and Y is hydrogen, and the rings
B and C are cis to each other, or (ii)
X and Y together are an additional bond,
or a pharmaceutically acceptable acid addition salt thereof.

2. A compound of claim 1 wherein X and Y are an additional bond.

3. A compound of claim 1 wherein X and Y are hydrogen.

4. A compound of claim 1 wherein $R_1$ and $R_2$ are hydrogen.

5. A compound of claim 1 wherein R is hydrogen, alkyl, alkenyl, alkynyl, alkyl substituted by cycloalkyl, hydroxyalkyl, phenylalkyl, phenylalkyl the phenyl thereof being substituted by halogen, alkoxy or alkyl, or A—CO—$R_3^{II}$ wherein A is alkylene and $R_3^{II}$ is alkyl, hydroxy, alkoxy, phenyl or halophenyl.

6. A compound of claim 5, wherein R is hydrogen, alkyl, alkenyl, alkynyl, alkyl substituted by cycloalkyl, halophenylalkyl, or —A—CO—$R_3^{II}$ as defined in claim 5.

7. A compound of claim 5, wherein R is —A—CO—$R_3^{III}$ wherein A is alkylene and $R_3^{III}$ is hydroxy.

8. A compound of claim 5, wherein R is alkyl of 1 to 3 carbon atoms, alkenyl or alkynyl of 3 carbon atoms, or hydroxyalkyl of 2 carbon atoms.

9. A compound of claim 5, wherein R is alkyl substituted by cycloalkyl of 3 to 4 carbon atoms.

10. A compound of claim 5, wherein R is phenylalkyl, wherein the phenyl moiety is substituted by halogen, alkoxy or alkyl.

11. A compound of claim 5, wherein R is —A—CO—$R_3^{IV}$ wherein A is alkylene and $R_3^{IV}$ is methyl, methoxy or ethoxy.

12. A compound of claim 5, wherein R is —A—CO—$R_3^{V}$ wherein A is alkylene and $R_3^{V}$ is phenyl or halophenyl.

13. A compound of claim 5, wherein A is ethylene or alkyl substituted ethylene.

14. A compound of claim 5, wherein $R_3^{II}$ is alkyl.

15. A compound of claim 1 which is (3aRS,4SR,9aSR)-3a,4,9,9a-tetrahydro-2-methyl-4-phenyl-benz[f]isoindoline.

16. A compound of claim 1 which is (3aRS,4SR,9aSR)-2-allyl-3a,4,9,9a-tetrahydro-4-phenyl-benz[f]isoindoline.

17. A compound of claim 1 which is (3aRS,4SR,9aSR)-2-cyclopropylmethyl-3a,4,9,9a-tetrahydro-4-phenyl-benz[f]isoindoline or the 4RS epimer thereof.

18. A compound of claim 1 which is (3aRS,4SR,9aSR)-3a,4,9,9a-tetrahydro-2-isopropyl-4-phenyl-benz[f]isoindoline or the 4RS epimer thereof.

19. A compound of claim 1 which is (3aRS,4SR,9aSR)-3a,4,9,9a-tetrahydro-4-phenyl-2-(2-propinyl)benz[f]isoindoline.

20. A compound of claim 1 which is (3aRS,4SR,9aSR)-2-(o-chlorophenethyl)-3a,4,9,9a-tetrahydro-4-phenyl-benz[f]isoindoline.

21. A compound of claim 1 which is (3aRS,4SR,9aSR)-2-(3a-4,9,9a-tetrahydro-4-phenyl-benz[f]isoindolin-2-yl)acetophenone or the 4RS epimer thereof.

22. A compound of claim 1 which is (3aRS,4SR,9aSR)-p-fluoro-4-(3a,4,9,9a-tetrahydro-4-phenyl-benz[f]isoindolin-2-yl)butyrophenone or the 4RS epimer thereof.

23. A compound of claim 1 which is (3aRS,4RS,9aSR)-3a,4,9,9a-tetrahydro-2-(p-methylbenzyl)-4-phenyl-benz[f]isoindoline or the 4RS epimer thereof.

24. A compound of claim 1 which is (3aRS,4SR,9aSR)-3a,4,9,9a-tetrahydro-2-(p-methoxybenzyl)-4-phenyl-benz[f]isoindoline.

25. A compound of claim 1 which is (3aRS,4SR,9aSR)-6-chloro-3a,4,9,9-tetrahydro-2-methyl-4-(4-chlorophenyl)benz[f]isoindoline.

26. A compound of claim 1 which is (3aRS,4SR,9aSR)-6-chloro-4-(4-chlorophenyl)-2-cyclopropylmethyl-3a,4,9,9a-tetrahydro-benz[f]isoindoline.

27. A compound of claim 1 which is (3aRS,4SR,9aSR)-2-acetonyl-6-chloro-4-(4-chlorophenyl)-3a,4,9,9a-tetrahydro-benz[f]isoindoline.

28. A compound of claim 1 which is (3aRS,4SR,9aSR)-7-chloro-4-(m-chlorophenyl)-3a,4,9,9a-tetrahydro-2-methyl-benz[f]isoindoline or the 4RS epimer thereof.

29. A compound of claim 1 which is (3aRS,4SR,9aSR)-2-acetonyl-7-chloro-4-(m-chlorophenyl)-3a,4,9,9a-tetrahydro-benz[f]isoindoline.

30. A compound of claim 1 which is (3aRS,4SR,9aSR)-7-chloro-4-(m-chlorophenyl)-2-cyclopropylmethyl-3a,4,9,9a-tetrahydro-benz[f]isoindoline or the 4RS epimer thereof.

31. A compound of claim which is (3aRS,4SR,9aSR)-3a,4,9,9a-tetrahydro-2,6-dimethyl-4-(p-tolyl)benz[f]isoindoline or the 4RS epimer thereof.

32. A compound of claim 1 which is (3aRS,4SR,9aSR)-2-cyclopropylmethyl-3a,4,9,9a-tetrahydro-6-methyl-4-(p-tolyl)benz[f]isoindoline or the 4RS epimer thereof.

33. A compound of claim 1 which is (3aRS,4SR,9aSR)-3a,4,9,9a-tetrahydro-6-methyl-2-(3-methyl-but-2-enyl)-4-(p-tolyl)benz[f]isoindoline.

34. A compound of claim 1 which is (3aRS,4SR,9aSR)-3a,4,9,9a-tetrahydro-2,6-dimethyl-4-phenyl-benz[f]isoindoline.

35. A compound of claim 1 which is (3aRS,4RS,9aSR)-2-acetonyl-3a,4,9,9a-tetrahydro-6-methyl-4-phenyl-benz[f]isoindoline.

36. A compound of claim 1 which is (3aRS,4SR,9aSR)-2-cyclopropylmethyl-3a,4,9,9a-tetrahydro-6-methyl-4-phenyl-benz[f]isoindoline or the 4RS epimer thereof.

37. A compound of claim 1 which is (3aRS,4SR,9aSR)-3a,4,9,9a-tetrahydro-2,7-dimethyl-4-phenyl-benz[f]isoindoline.

38. A compound of claim 1 which is (3aRS,4SR,9aSR)-2-acetonyl-3a,4,9,9a-tetrahydro-7-methyl-4-phenyl-benz[f]isoindoline.

39. A compound of claim 1 which is (3aRS,4SR,9aSR)-2-cyclopropylmethyl-3a,4,9,9a-tetrahydro-7methyl-4-phenyl-benz[f]isoindoline or the 4RS epimer thereof.

40. A compound of claim 1 which is (3aRS,4SR,9aSR)-3a,4,9,9a-tetrahydro-7-methyl-4-phenyl-benz[f]isoindolin-2-yl)-p-fluoroacetophenone or the 4RS epimer thereof.

41. A compound of claim 1 which is (3aRS,4SR,9aSR)-6-chloro-3a,4,9,9a-tetrahydro-2-methyl-4-phenyl-benz[f]isoindoline or the 4RS epimer thereof.

42. A compound of claim 1 which is (3aRS,4SR,9aSR)-3a,4,9,9a-tetrahydro-2-(3-methylbut-2-enyl)-4-phenyl-benz[f]isoindoline.

43. A compound of claim 1 which is (3aRS,4RS,9aSR)-3a,4,9,9a-tetrahydro-6-methyl-2-(3-methylbut-2enyl)-4-phenyl-benz[f]isoindoline.

44. A compound of claim 1 which is (3aRS,4SR,9aSR)-3a,4,9,9a-tetrahydro-6-methyl-4-phenyl-2-(2-propinyl)-benz[f]isoindoline.

45. A compound of claim 1 which is (3aRS,4RS,9aSR)-6-chloro-2-cyclopropylmethyl-3a,4,9,9a-tetrahydro-4-phenyl-benz[f]isoindoline.

46. A compound of claim 1 which is (3aRS,4SR,9aSR)-6-chloro-3a,4,9,9-tetrahydro-4-phenyl-2-(2-propinyl)-benz[f]isoindoline.

47. A compound of claim 1 which is (3aRS,4SR,9aSR)-6-chloro-3a,4,9,9a-tetrahydro-2-(3-methylbut-2-enyl)-4-phenyl-benz[f]isoindoline.

48. A compound of claim 1 which is (3aRS,4RS,9aSR)-6-chloro-2-ethyl-3a,4,9,9a-tetrahydro-4-phenyl-benz[f]isoindoline.

49. A compound of claim 1 which is (3aRS,4SR,9aSR)-2-n-butyl-6-chloro-3a,4,9,9a-tetrahydro-4-phenyl-benz[f]isoindoline.

50. A compound of claim 1 which is (3aRS,4SR,9aSR)-6-chloro-2-isopropyl-3a,4,9,9a-tetrahydro-4-phenyl-benz[f]isoindoline.

51. A compound of claim 1 which is (3aRS,4SR,9aSR)-2-(but-2-inyl)-3a,4,9,9a-tetrahydro-4-phenyl-benz[f]isoindoline.

52. A compound of claim 1 which is (3aRS,4RS,9aSR)-3a,4,9,9a-tetrahydro-2-methyl-4-phenyl-benz[f]isoindoline.

53. A compound of claim 1 which is (3aRS,4RS,9aSR)-2-acetonyl-3a,4,9,9a-tetrahydro-4-phenyl-benz[f]-isoindoline or the 3a,4 dehydro analogue thereof.

54. A compound of claim 1 which is (3aRS,4RS,9aSR)-3a,4,9,9a-tetrahydro-2,6-dimethyl-4-phenyl-benz[f]isoindoline or the 3a, 4 dehydro analogue thereof.

55. A compound of claim 1 which is (3aRS,4RS,9aSR)-3a,4,9,9a-tetrahydro-2,7-dimethyl-4-phenyl-benz[f]isoindoline or the 3a,4 dehydro analogue thereof.

56. A compound of claim 1 which is (3aRS,4RS,9aSR)-2-benzyl-6-chloro-3a,4,9,9a-tetrahydro-4-phenyl-benz[f]isoindoline.

57. A compound of claim 1 which is (9aRS)-2-benzyl-9,9a-dihydro-6-methyl-4-phenyl-benz-[f]-isoindoline.

58. A compound of claim 1 which is (9aRS)-9,9a-dihydro-2-methyl-4-phenyl-3-benz[f]isoindoline.

59. A compound of claim 1 which is (9aRS)-2-benzyl-9,9a-dihydro-7-methyl-4-phenyl-benz[f]isoindoline.

60. A compound of claim 1 which is (9aRS)-2-benzyl-9,9a-dihydro-4-phenyl-benz[f]isoindoline.

61. A compound of claim 1 which is (9aRS)-2-benzyl-6-chloro-9,9a-dihydro-4-phenyl-benz[f]isoindoline.

62. A compound of claim 1 which is (3aRS, 4SR,9aSR)-4-(3a,4,9,9a-tetrahydro-4-phenyl-benz[f]-isoindoline-2-yl)-2-butanone.

63. A compound of claim 1 which is (3aRS, 4SR,9aSR)-3a,4,9,9a-tetrahydro-4-phenyl-benz[f]-isoindoline-2-propionic acid methyl ester.

64. A compound of claim 1 which is (3aRS,4SR,9aSR)-3a,4,9,9a-tetrahydro-4-phenyl-benz[f]isoindoline-2-propionic acid, 65. A compound of claim 1 which is (3aRS,4SR,9aSR)-2-(2-hydroxyethyl)-3a,4,9,9a-tetrahydro-6-methyl-4-(p-tolyl)-2-benz[f]isoindoline or the 4RS epimer thereof.

66. A compound of claim 1 which is 4-[(9aRS)-9,9a-dihydro-4-phenyl-benz[f]isoindolin-2-yl]-butan-2-one.

67. A compound of claim 1 which is [(9aRS)-9,9a-dihydro-4-phenyl-benz[f]isoindolin-2-yl]-propionic acid.

68. A compound of claim 1 which is (3aRS,4SR,9aSR)-3a,4,9,9a-tetrahydro-4-phenyl-benz[f]isoindoline or the 4RS epimer thereof.

69. A compound of claim 1 which is (3aRS,4SR,9aSR)-6-chloro-4-(4-chlorophenyl)-3a,4,9,9a-tetrahydro-benz[f]isoindoline or the 4RS epimer thereof.

70. A compound of claim 1 which is (3aRS,4SR,9aSR)-6-fluoro-4-(p-fluoro-phenyl)-3a,4,9,9a-tetrahydro-benz[f]isoindoline or the 4RS epimer thereof.

71. A compound of claim 1 which is (3aRS,4SR,9aSR)-7-chloro-4-(m-chlorophenyl)-3a,4,9,9a-tetrahydro-benz[f]isoindoline or the 4RS epimer thereof.

72. A compound of claim 1 which is (3aRS,4SR,9aSR)-3a,4,9,9a-tetrahydro-6-methyl-4-(p-tolyl) benz[f]isoindoline or the 4RS epimer thereof.

73. A compound of claim 1 which is (3aRS,4SR,9aSR)-3a,4,9,9a-tetrahydro-6-methyl-4-phenyl-benz[f]isoindoline or the 4RS epimer thereof.

74. A compound of claim 1 which is (3aRS,4SR,9aSR)-3a,4,9,9a-tetrahydro-7-methyl-4-phenyl-benz[f]isoindoline or the 4RS epimer thereof.

75. A compound of claim 1 which is (3aRS,4SR,9aSR)-6-chloro-3a,4,9,9a-tetrahydro-4-phenyl-benz[f]isoindoline.

76. A compound of claim 1 which is (3aRS,4RS,9aSR)-3a,4,9,9a-tetrahydro-4-phenyl-benz[f]isoindoline.

77. A compound of claim 1 which is (3aRS,4RS,9aSR)-3a,4,9,9a-tetrahydro-6-methyl-4-phenyl-benz[f]isoindoline.

78. A compound of claim 1 which is (3aRS,4RS,9aSR)-3a,4,9,9a-tetrahydro-7-methyl-4-phenyl-benz[f]isoindoline.

79. A compound of claim 1 which is (3aRS,4RS,9aSR)-6-chloro-3a,4,9,9a-tetrahydro-4-phenyl-benz[f]isoindoline.

80. A compound of claim 1 which is (9aRS)-9,9a-dihydro-4-phenyl-benz[f]isoindoline.

81. A compound of claim 1 which is (3aRS,4SR,9aSR)-2-acetonyl-3a,4,9,9a-tetrahydro-4-phenyl-benz[f]isoindoline.

82. A compound of claim 1 which is (3aRS,4SR,9aSR-2-(but-2-inyl)-3a, 4,9,9a-tetrahydro-4-phenyl-benz[f]isoindoline.

83. A compound according to claim 5, wherein $R_4$ is $A-CO-R_3^{II}$ as defined in claim 5.

84. A compound according to claim 83 wherein $R_3^{II}$ is alkoxy.

85. A compound of claim 5 wherein R is alkyl of 1 to 3 carbon atoms.

86. A compound of claim 5, wherein R is alkynyl, alkyl substituted by cycloalkyl, or $-A-CO-R_3^{II}$ wherein $R_3^{II}$ is alkyl, hydroxy or alkoxy.

87. A compound of claim 5 wherein R is alkynyl, alkyl substituted by cycloalkyl, or $-A-CO-R_3^{II}$ wherein $R_3^{II}$ is alkyl, hydroxy, alkoxy or halophenyl.

88. A compound of claim 5, wherein R is alkynyl, alkyl substituted by cycloalkyl, or $-A-CO-R_3^{II}$ wherein $R_3^{II}$ is alkyl, hydroxy, alkoxy or phenyl.

89. A compound of claim 1, wherein R is phenylalkyl, the phenyl thereof being substituted by halogen, alkoxy or alkyl.

90. A compound according to claim 1 wherein $R_2$ is alkyl.

91. A compound according to claim 1 wherein $R_2$ is halogen.

92. A compound of claim 1 in the 3aRS,4SR,9aSR form substantially free from its optical antipode.

93. (3aRS, 4SR, 9aSR)-3a4,9,9a,-tetrahydro-4-phenylbenz[f]isoindoline-2-trifluoroacetamide.

94. A compound of claim 1 of formula

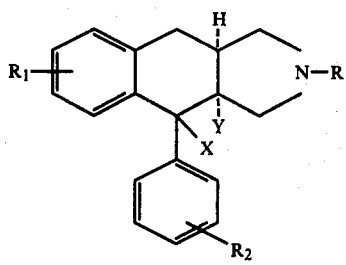

wherein
each of X and Y is hydrogen,
R₁ is hydrogen, halogen or alkyl,
R₂ is hydrogen, and
R is
(i) hydrogen
(ii) alkyl of 1 to 5 carbon atoms
(iii) alkenyl of 3 to 5 carbon atoms, the multiple bond thereof being in other than the α position,
(iv) hydroxy-alkyl of 2 to 5 carbon atoms,
(v) phenylalkyl of 7 to 11 carbon atoms in the aggregate thereof,
(vi) —A—CO—R₃
wherein
A is alkylene of 1 to 4 carbon atoms, and
R₃ is phenyl or phenyl substituted by halogen.

95. A pharmaceutical composition for treating depression comprising an anti-depression effective amount of a compound of claim 94 with a pharmaceutical carrier or diluent.

96. A method of treating depression in animals, which comprises administering an anti-depression effective amount of a compound of claim 1 to an animal in need of such treatment.

97. A compound of claim 1 having the formula

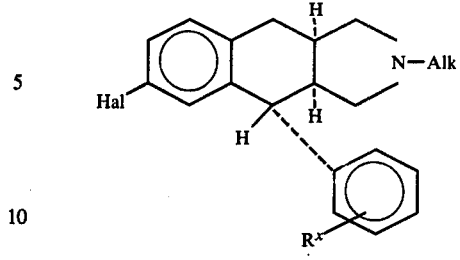

wherein
Hal is halogen and
Alk is alkyl of 1 to 5 carbon atoms and
$R^x$ is halogenor alkyl of 1 to 4 carbon atoms.

98. The compound of claim 1 which is (3aRS,4SR,9aSR)-6-chloro-4-(m-chlorophenyl)-3a,4,9,9a-tetrahydro-2-methyl-benz[f]isoindoline.

99. The compound of claim 1 which is (3aRS,4RS,9aRS)-6-chloro-4-(o-chlorophenyl)-3a,4,9,9a-tetrahydro-2-methyl-benz[f]isoindoline.

100. The compound of claim 1 which is (3aRS,4RS,9aSR)-6-chloro-3a,4,9,9a-tetrahydro-2-methyl-4-(o-tolyl)-benz[f]isoindoline.

101. The compound of claim 1 which is (3aRS,4SR,9aSR)-6-chloro-3a,4,9,9a-tetrahydro-2-methyl-4(m-tolyl)-benz[f]isoindoline.

102. The compound of claim 1 which is (3aRS,4RS,9aSR)-6-chloro-3a,4,9,9a-tetrahydro-2-methyl-4-(p-tolyl)-benz[f]isoindoline.

103. The compound of claim 1 which is (3aRS,4SR,9aSR)-4-(p-ethylphenyl)-6-chloro-3a,4,9,9a-tetrahydro-2-methyl-benz[f]isoindoline.

104. The compound of claim 1 which is (3aRS,4SR,9aSR)-4-(p-bromophenyl)-6-chloro-3a,4,9,9a-tetrahydro-2-methyl-benz[f]isoindoline.

105. The compound of claim 1 which is (3aRS,4SR,8SR)-6-chloro-4-(p-fluorophenyl)-3a,4,9,9a-tetrahydro-2-methyl-benz[f]isoindoline.

106. A compound of claim 1 in the 3aRS,4RS,9aSR form substantially free from its optical antipode.

* * * * *

UNITED STATES PATENT AND TRADEMARK OFFICE
CERTIFICATE OF CORRECTION

PATENT NO. : 4,171,369
DATED : March 17, 1975
INVENTOR(S) : ROLAND ACHINI ET AL

It is certified that error appears in the above—identified patent and that said Letters Patent is hereby corrected as shown below:

Col. 2 line 62 after the word "of" delete "120°-"

Col. 10 line 16 after the word "or" delete the letter "P"

Delete the formula in abstract and insert in its place this corrected formula

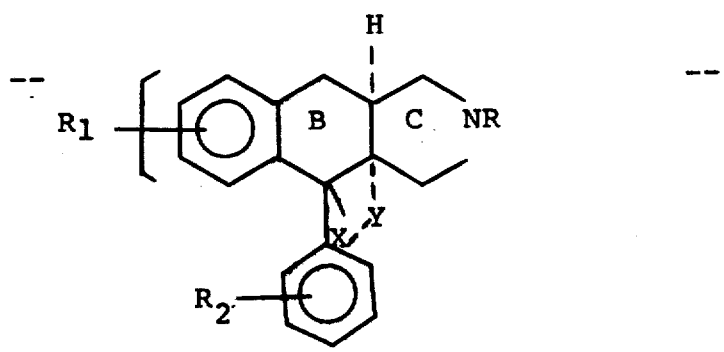

Signed and Sealed this

Fifth Day of August 1980

[SEAL]

Attest:

SIDNEY A. DIAMOND

Attesting Officer

Commissioner of Patents and Trademarks